US010738152B2

(12) United States Patent
Wang et al.

(10) Patent No.: US 10,738,152 B2
(45) Date of Patent: Aug. 11, 2020

(54) METHODS OF ELECTROSPINNING AND COMPOSITIONS MADE THEREFROM

(71) Applicant: UNIVERSITY OF PITTSBURGH—OF THE COMMONWEALTH SYSTEM OF HIGHER EDUCATION, Pittsburgh, PA (US)

(72) Inventors: Yadong Wang, Allison Park, PA (US); Eric M. Jeffries, Pittsburgh, PA (US); Robert A. Allen, Pittsburgh, PA (US)

(73) Assignee: Univeristy of Pittsburgh—Of the Commonwealth System of Higher Education, Pittsburgh, PA (US)

(*) Notice: Subject to any disclaimer, the term of this patent is extended or adjusted under 35 U.S.C. 154(b) by 167 days.

(21) Appl. No.: 15/904,863

(22) Filed: Feb. 26, 2018

(65) Prior Publication Data
US 2018/0251596 A1 Sep. 6, 2018

Related U.S. Application Data

(62) Division of application No. 14/652,744, filed as application No. PCT/US2013/077226 on Dec. 20, 2013, now Pat. No. 9,938,373.
(Continued)

(51) Int. Cl.
A61L 27/18 (2006.01)
C08G 63/91 (2006.01)
(Continued)

(52) U.S. Cl.
CPC ............. *C08G 63/916* (2013.01); *A61F 2/82* (2013.01); *A61K 47/34* (2013.01); *A61L 27/18* (2013.01);
(Continued)

(58) Field of Classification Search
CPC ........... A61L 27/14; A61L 27/18; A61L 27/26
See application file for complete search history.

(56) References Cited

U.S. PATENT DOCUMENTS 8,048,446 B2 11/2011 Lelkes et al.
2009/0011486 A1 1/2009 Bettinger et al.
(Continued)

FOREIGN PATENT DOCUMENTS

WO WO 2012-015623 2/2012
WO WO 2012-078472 6/2012

OTHER PUBLICATIONS

Yi et al. (2008). Poly(glycerol sebacate) Nanofiber Scafoolds by Core/Shell Electrospinning. Macromol. Biosci., vol. 8, pp. 803-806. (Year: 2008).*
(Continued)

Primary Examiner — Suba Ganesan
(74) Attorney, Agent, or Firm — Klarquist Sparkman, LLP

(57) ABSTRACT

Disclosed herein are methods of electrospinning poly(glycerol sebacate) (PGS) which allow stable PGS fibers and fibrous PGS constructs, scaffolds and grafts to be formed. In one example, a disclosed method includes generating PGS fibers by blending PGS prepolymer with a heat resistant synthetic carrier polymer, wherein the blend is electrospun into micro- or nano-fibers, and the PGS prepolymer is cross-linked into PGS with heat without using chemical cross-linkers. In another example, a disclosed method includes electrospinning a PGS and gelatin blend, wherein the PGS and gelatin composition are cross-linked by heat curing without using chemical cross-linkers. In another example, the method includes preparing an electrospinning precursor solution comprising blending PGS prepolymer with poly(lactic-co-glycolic acid) (PLGA) and a chemical
(Continued)

cross-linker; electrospinning the prepared blend; and exposing the electrospun blend to an organic solvent to remove the PLGA.

11 Claims, 29 Drawing Sheets

Related U.S. Application Data

(60) Provisional application No. 61/745,380, filed on Dec. 21, 2012.

(51) Int. Cl.
*A61K 47/34* (2017.01)
*A61F 2/82* (2013.01)
*D01D 5/00* (2006.01)
*D01D 10/02* (2006.01)
*D01F 6/62* (2006.01)

(52) U.S. Cl.
CPC ........... *D01D 5/003* (2013.01); *D01D 5/0007* (2013.01); *D01D 5/0038* (2013.01); *D01D 10/02* (2013.01); *D01F 6/62* (2013.01); *A61F 2230/0069* (2013.01); *A61F 2250/0067* (2013.01)

(56) References Cited

U.S. PATENT DOCUMENTS

| | | |
|---|---|---|
| 2009/0221047 A1 | 9/2009 | Schindler et al. |
| 2010/0055184 A1 | 3/2010 | Zeitels et al. |
| 2010/0233115 A1 | 9/2010 | Petel et al. |
| 2011/0236974 A1 | 9/2011 | Ogle et al. |
| 2014/0079759 A1 | 3/2014 | Patel et al. |
| 2014/0309726 A1* | 10/2014 | Wang ................. A61L 27/56 623/1.46 |
| 2015/0272729 A1 | 10/2015 | Wagner et al. |

OTHER PUBLICATIONS

Ifkovits et al., "Biodegradable fibrous scaffolds with tunable properties formed from photo-cross-linkable poly(glycerol sebacate)," *ACS Appl. Mater. Interfaces*, 2, (9), 1878-86, 2009.

Kenar et al., "Design of a 3D aligned myocardial tissue construct from biodegradable polyesters," *Master Sci.: Master Med.*, vol. 21, pp. 989-997, 2010.

Ravichandran et al., "Poly(Glycerol sebacate)/gelatin core/shell fibrous structure for regeneration of myocardial infarction," *Tissue Eng. Part A*, 17, (9-10), 1363-73, 2011.

Sant et al., "Hybrid PGS-PCL microfibrous scaffolds with improved mechanical and biological properties," *J Tissue Eng. Regen. Med.*, 2010.

Yi et al., "Poly(glycerol sebacate) nanofiber scaffolds by core/shell electrospinning," *Macromol. Biosci.*, 8, (9), 803-6, 2008.

* cited by examiner

FIG. 2
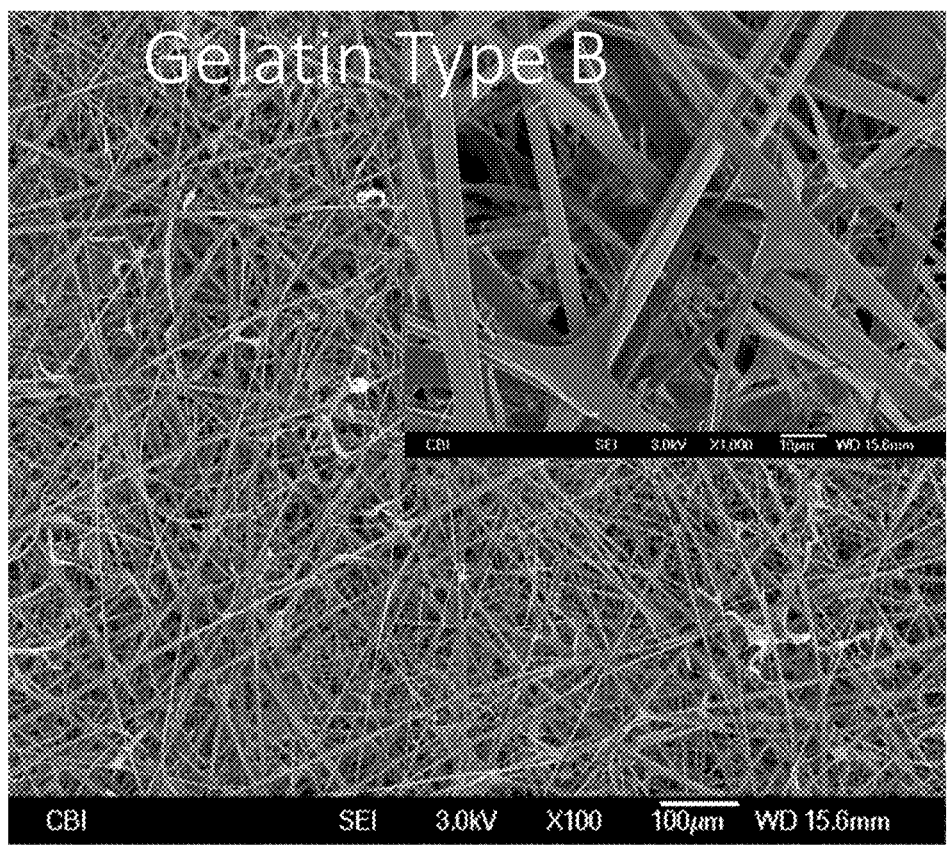
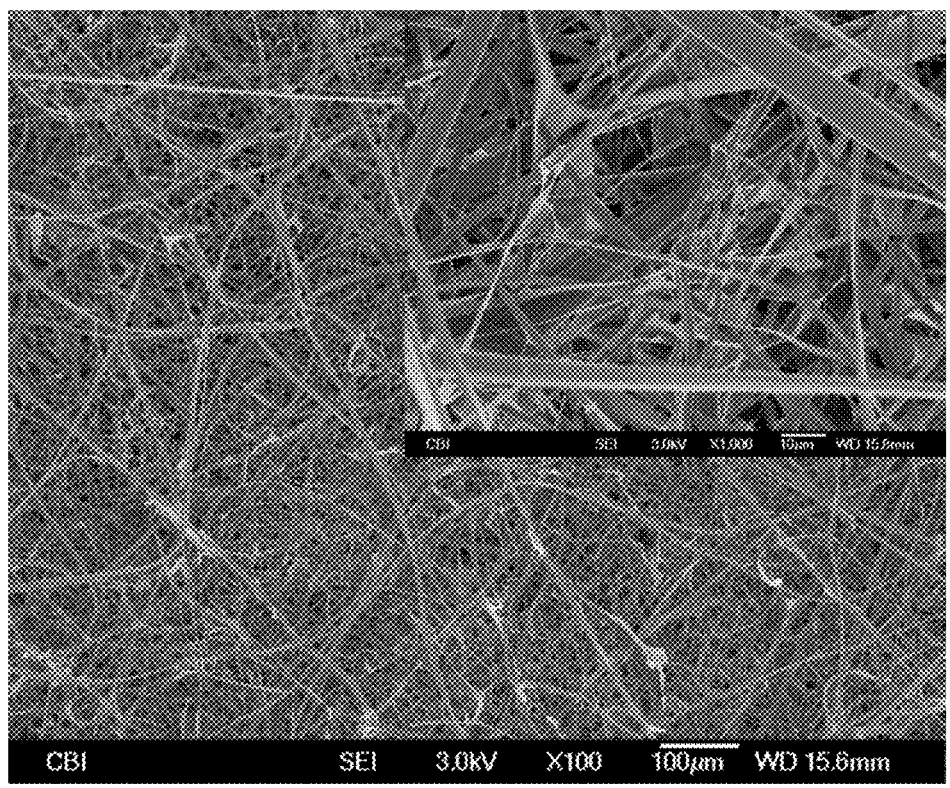
Post cured 130-24hr

FIG. 3
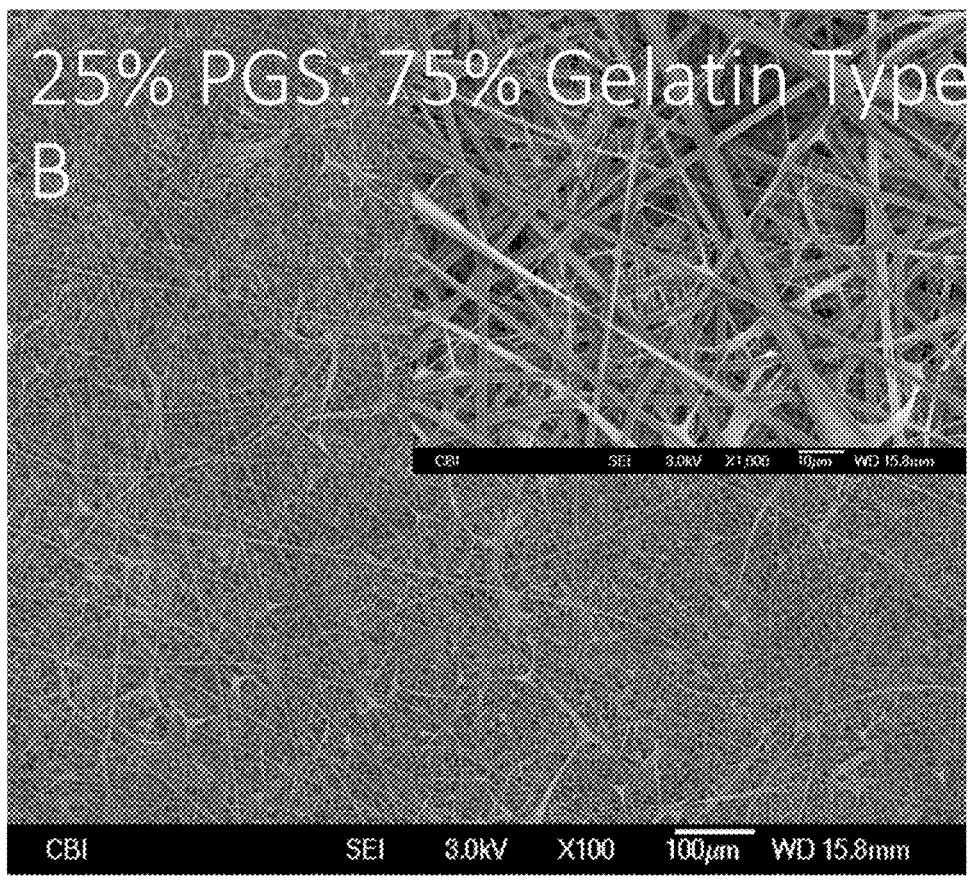
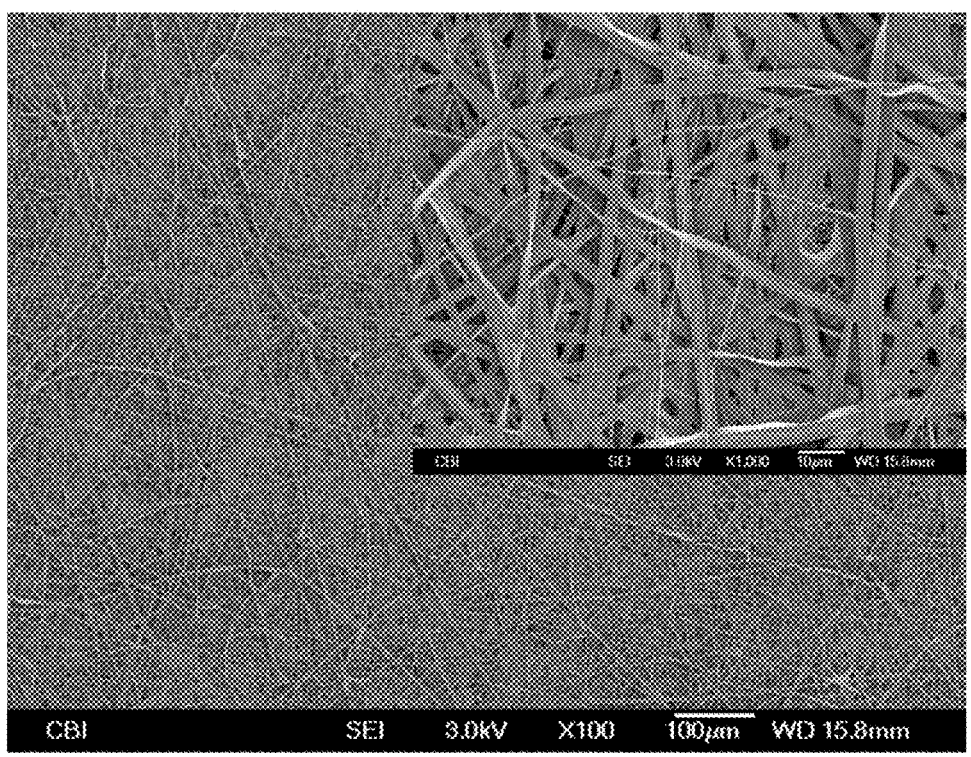
Post cured 130-24hr

FIG. 4
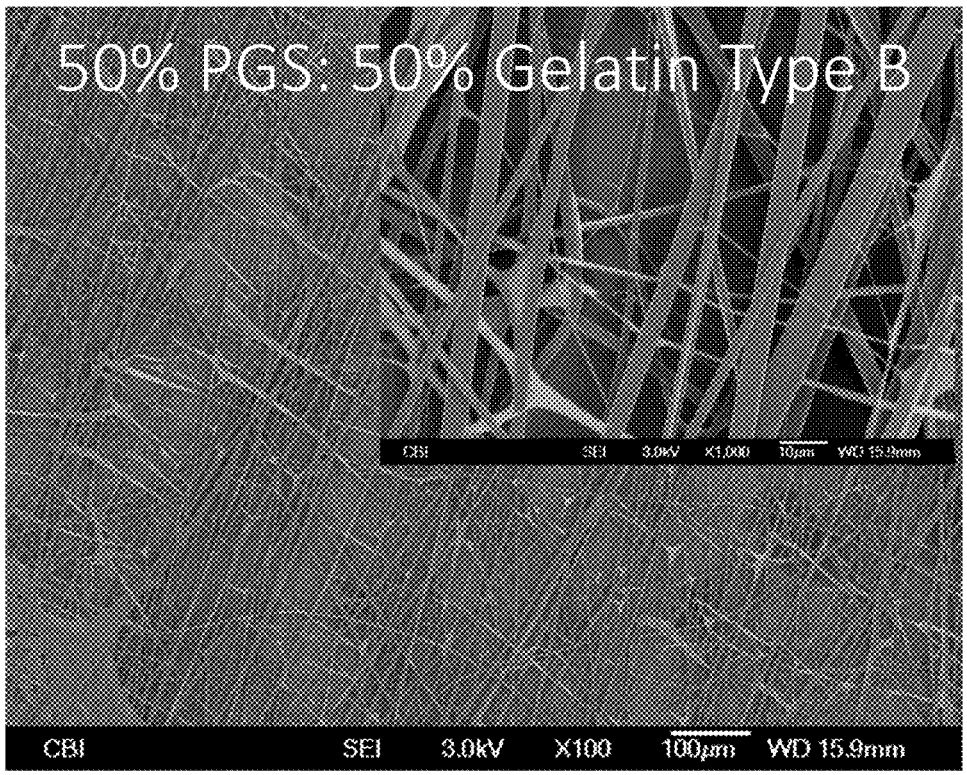
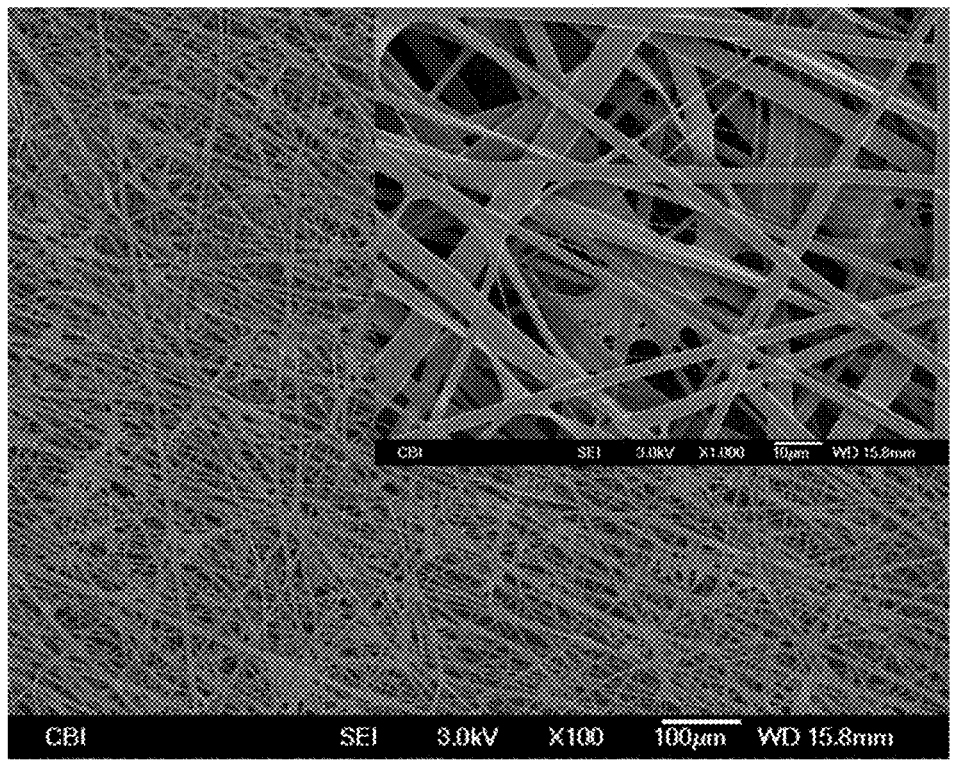
Post cured 130-24hr

Post cured 130-24hr

Post cured 130-24hr

Post cured 130-24hr

Post cured 130-24hr

Post cured 130-24hr

FIG. 10A
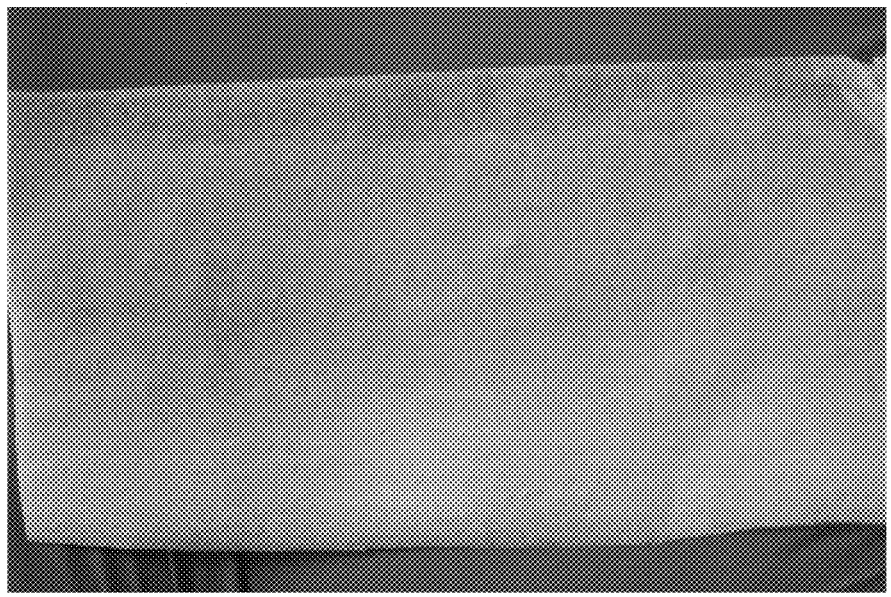
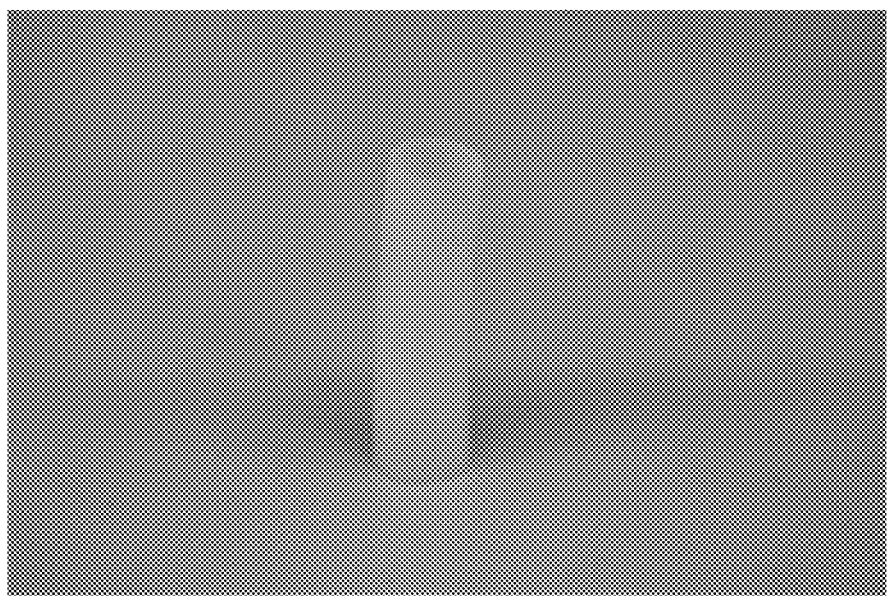
FIG. 10B

71% PGS:29% gelatin B
to mandrel

77% PGS:23% gelatin B
to mandrel

FIG. 15A
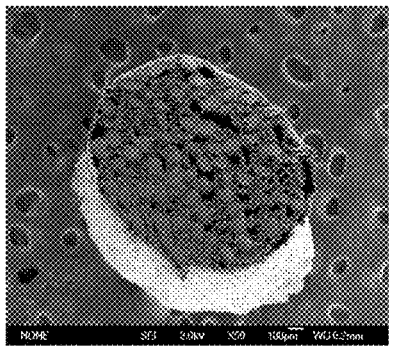
FIG. 15B
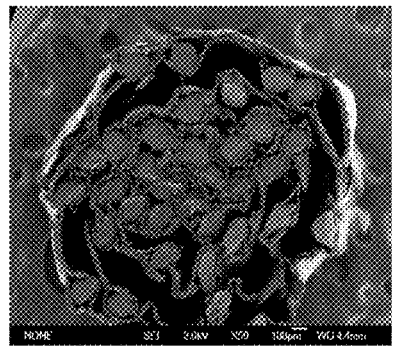
FIG. 15C
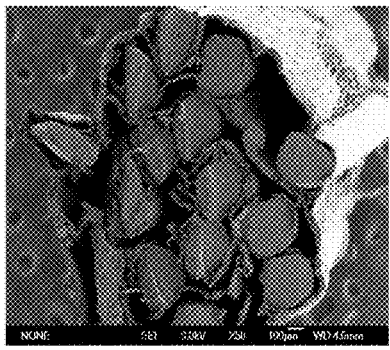
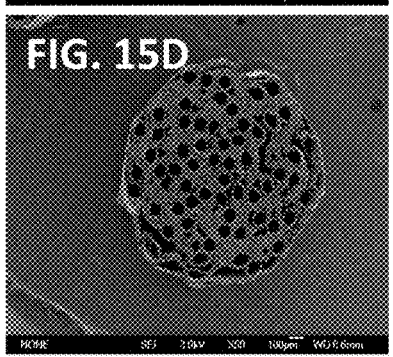
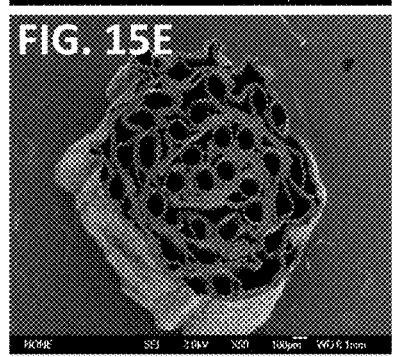
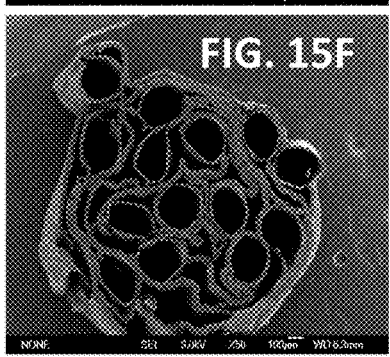
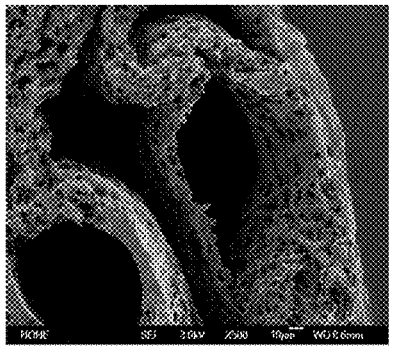
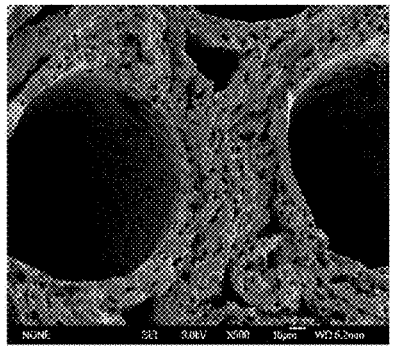
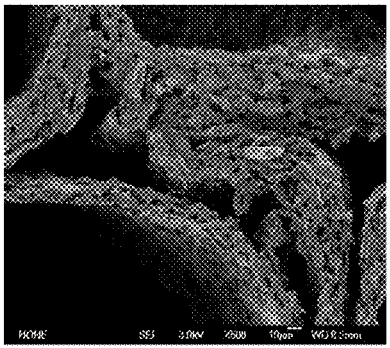
FIG. 15G
FIG. 15H
FIG. 15I
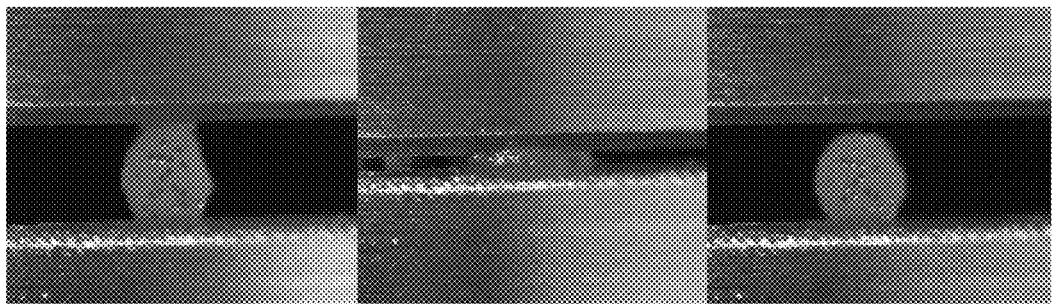
FIG. 15J
FIG. 15K
FIG. 15L

FIG. 17
SEM after autoclave
63% PGS 37% Gelatin
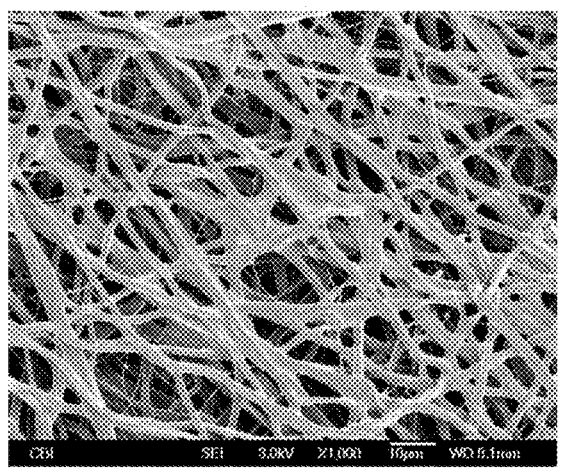
Cured: 130°C-24hr
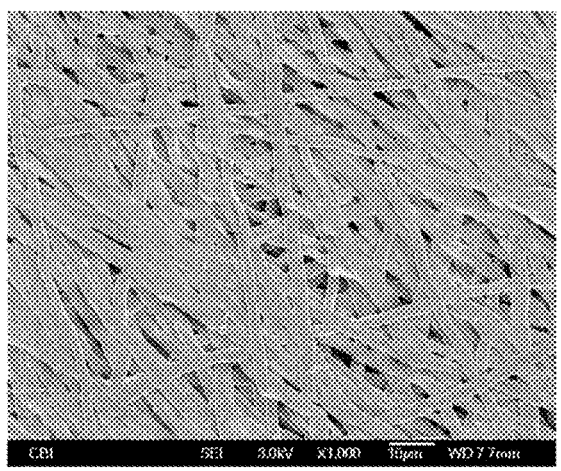
No curing
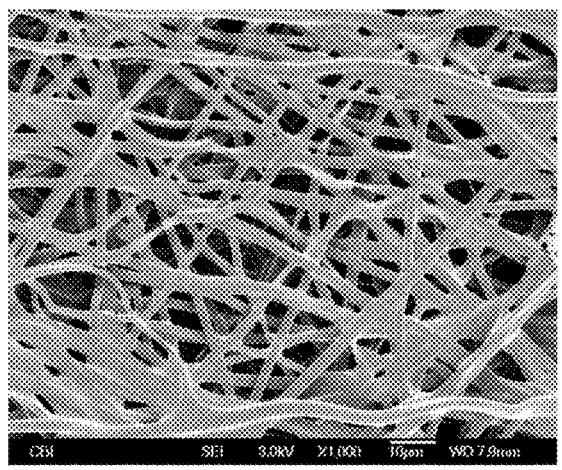
Cured: 150°C-24hr

FIG. 18

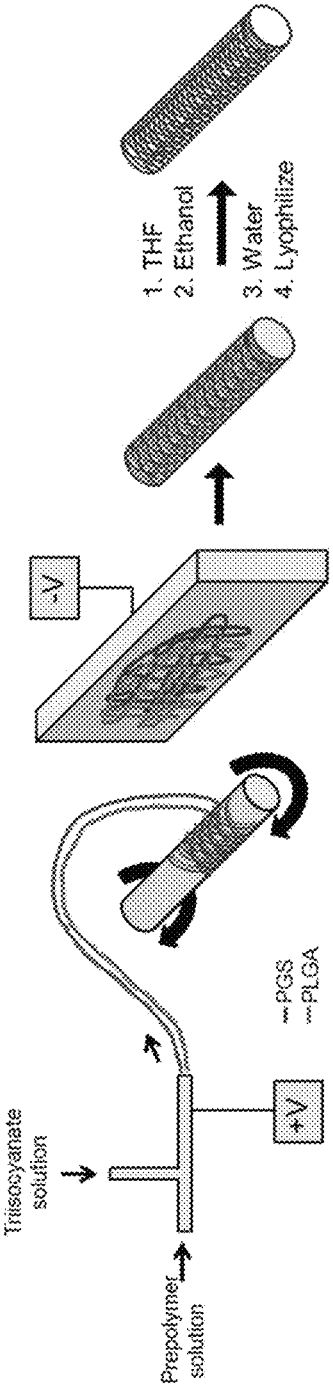

Electrospin our unique precursor solution containing PGS, PLGA, and lysine triisocyanate onto a glucose rod. Can make the final PGS tube any size by adjusting the size of the glucose rod Dissolve the glucose rod in water to free the graft, then dissolve PLGA with organic solvents 1. THF
2. Ethanol
3. Water
4. Lyophilize Finished product can be sterilized by standard methods: autoclave or ethylene oxide gas Finished product

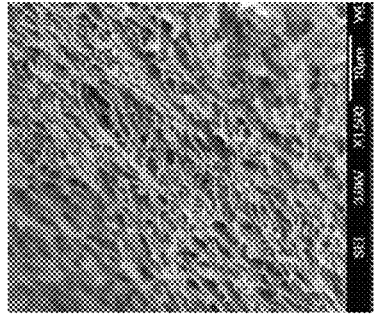

Magnified inner surface of PGS tube

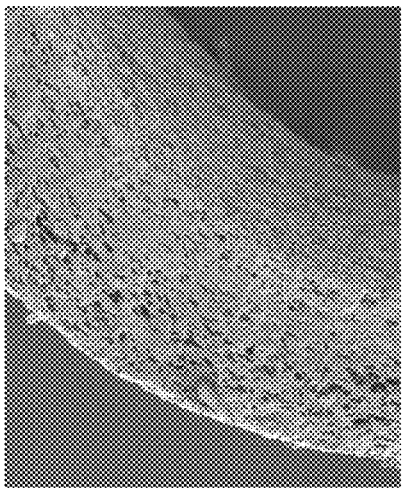

Magnified wall of PGS tube

Abbreviations:
PGS – poly(glycerol sebacate)
PLGA – poly(lactic-co-glycolic acid)
THF – Tetrahydrofuran (organic solvent)

FIG. 20
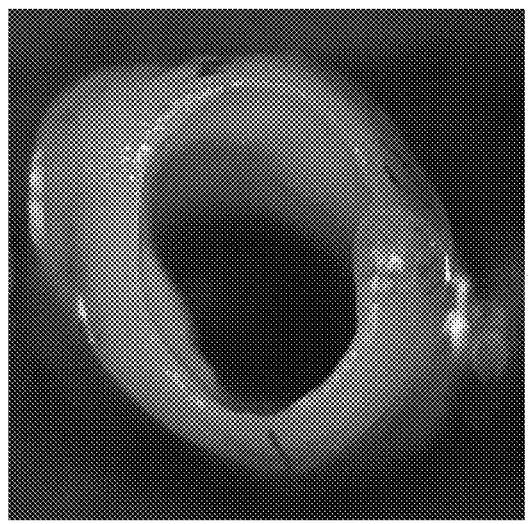
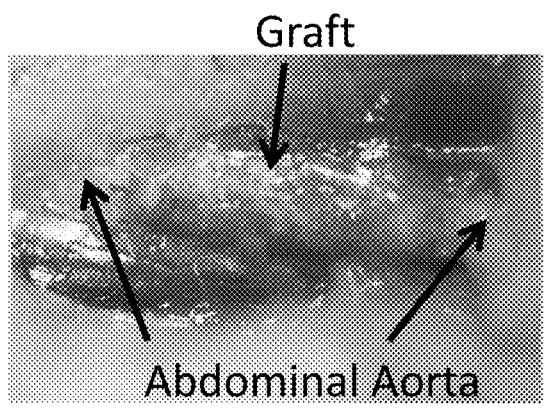
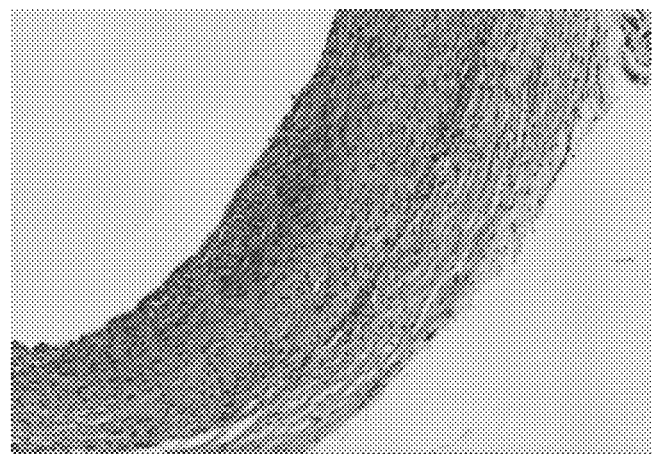

55:45 PGS:PVA as electrospun → Cured at 120°C-24hrs

FIG. 24
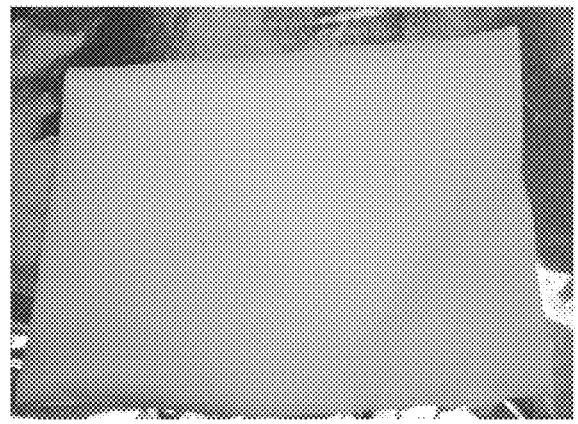
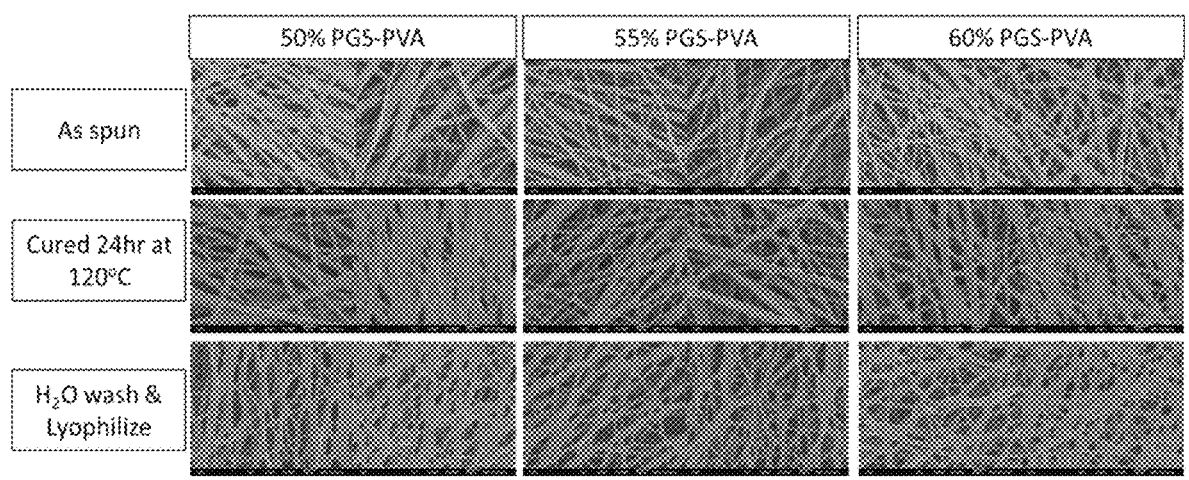

C=O peak at 1740 (specific to PGS) increases after washing to value close to PGS alone

| Pink | 55PGS-PVA as spun |
|---|---|
| Light blue | 1) then crosslinked at 120°C for 48hrs |
| Blue | 2) then ethanol/water wash, then lyophilized |
| Purple | PVA pellet |
| Red | PGS film 120°C for 48hrs- ethanol/water wash |

| Electrospun solution PGS% by mass | 55% |
|---|---|
| Mass after ethanol/water wash | 54.24% |

FIG. 26
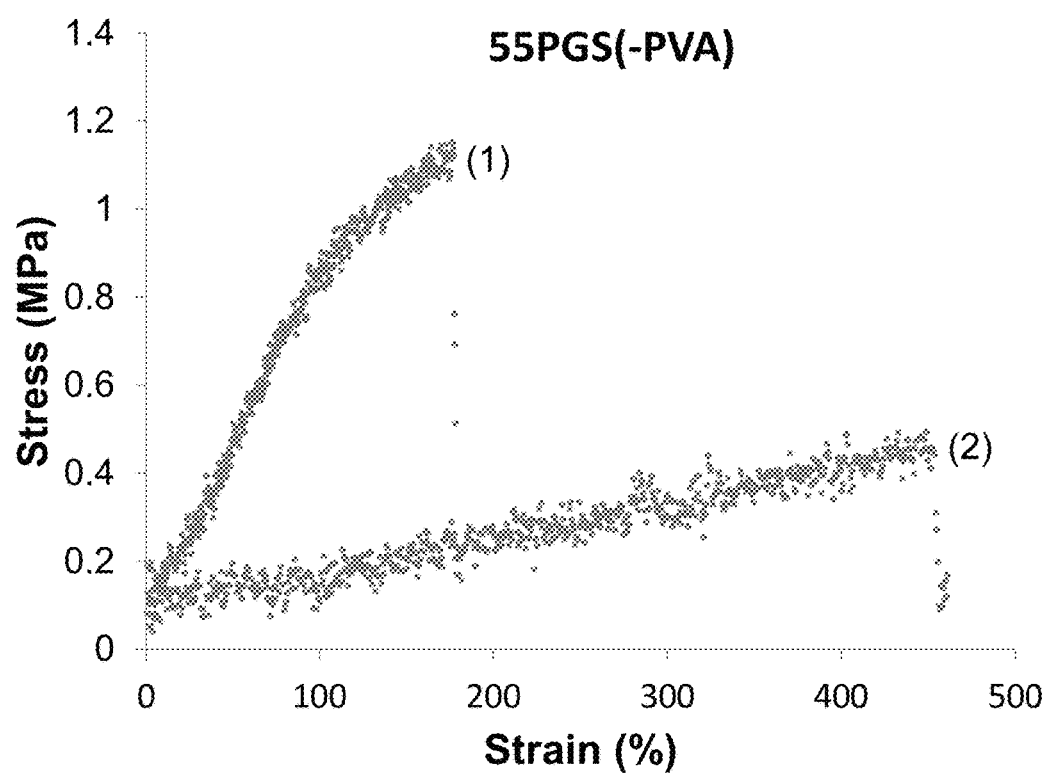
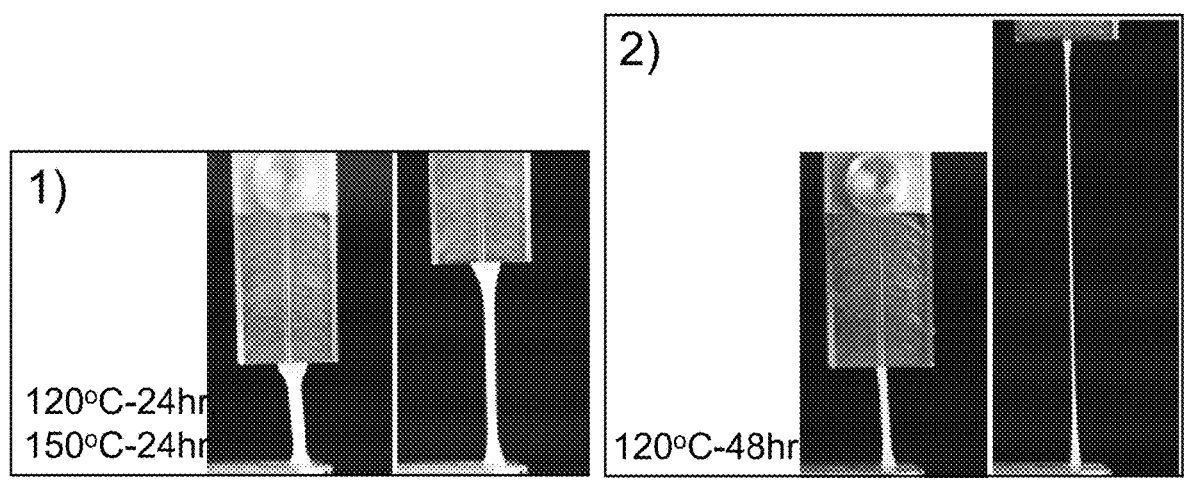

FIG. 27A            FIG. 27B
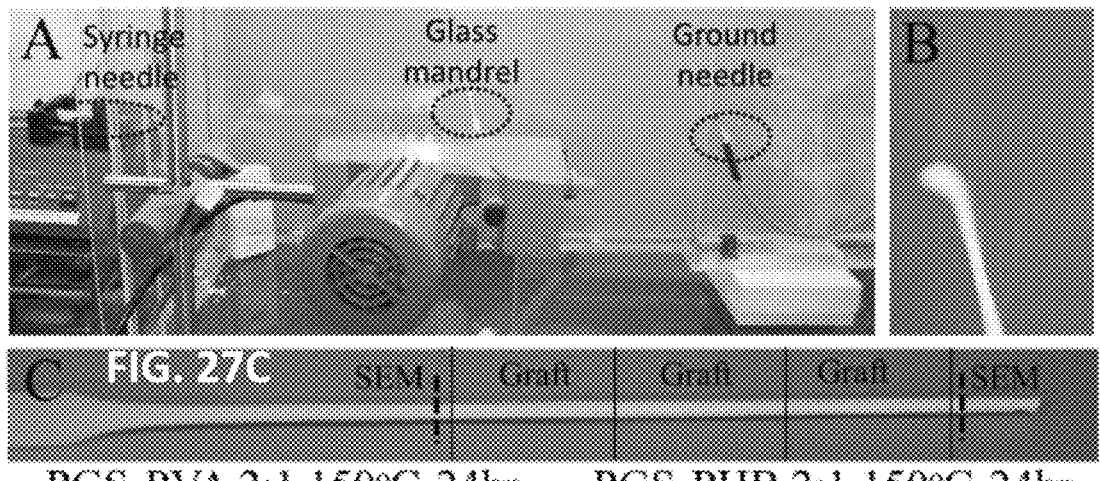
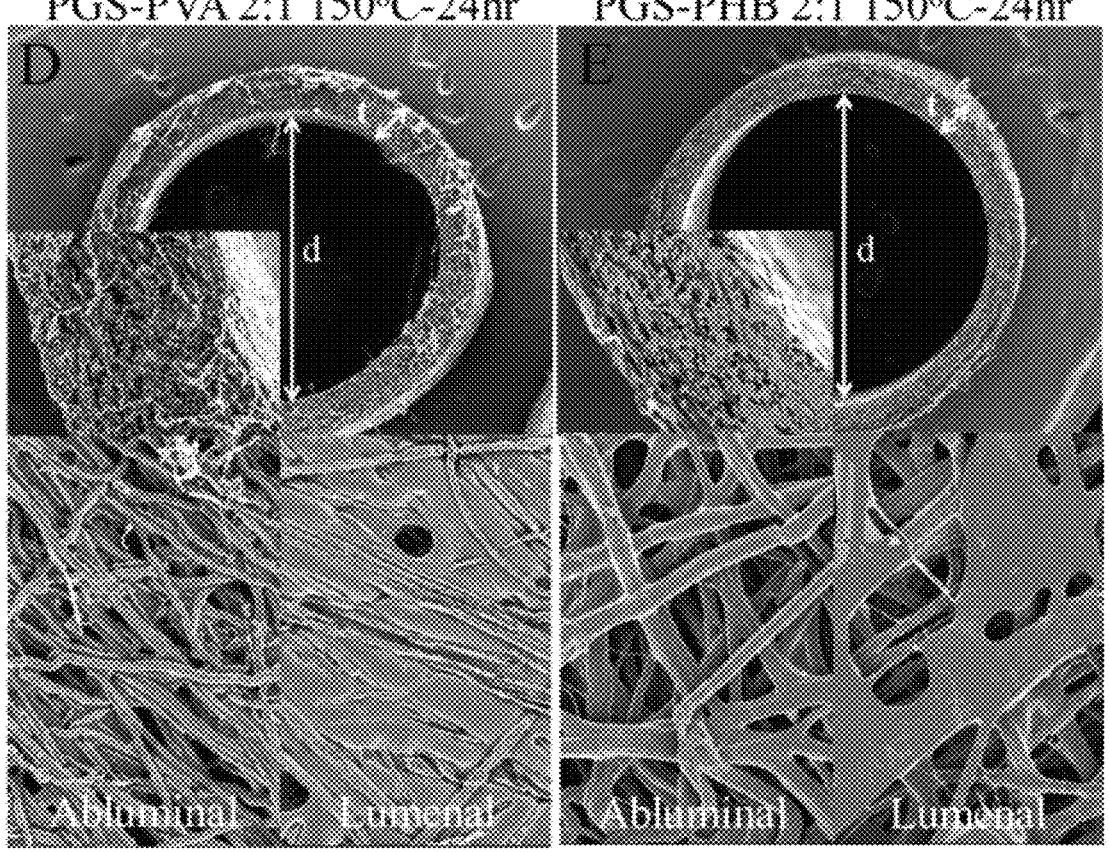
FIG. 27D            FIG. 27E

METHODS OF ELECTROSPINNING AND COMPOSITIONS MADE THEREFROM

CROSS REFERENCE TO RELATED APPLICATION

This application is a divisional of U.S. patent application Ser. No. 14/652,744, filed Jun. 16, 2015, which is the § 371 U.S. National Stage of International Application No. PCT/US2013/077226, filed Dec. 20, 2013, which was published in English under PCT Article 21(2), which in turn claims the benefit of U.S. Provisional Patent Application No. 61/745,380, filed Dec. 21, 2012, all of which applications are incorporated herein by reference in their entirety.

ACKNOWLEDGMENT OF GOVERNMENT SUPPORT

This invention was made with government support under HL089658 and HL076124 awarded by the National Institutes of Health. The government has certain rights in the invention.

FIELD

This disclosure relates to methods of electrospinning poly(glycerol sebacate), with or without another polymer, and compositions made therefrom, such as fibrous constructs which can be used as tissue engineering scaffolds, including for the replacement and/or repair of damaged native tissues.

BACKGROUND

Amongst various polymers, the biocompatible and biodegradable elastomer, poly(glycerol-sebacate) (PGS) has shown great promise in soft tissue scaffolding. PGS can be easily synthesized from glycerol and sebacic acid. Biocompatibility studies of PGS have shown excellent compatibility with a wide range of cells and tissues both in vitro and in vivo. However, PGS processability into nano-/microfibers still remains problematic. Fibrous scaffolds are considered advantageous for tissue engineering due to at least their extracellular matrix (ECM) mimicking properties, high surface area to volume ratio and anisotropic mechanical properties. The contact guidance provided by these fibers can be used to regulate cell orientation and migration. Fibrous scaffolds also have improved mechanical strength and suture retention compared to other scaffold structures, making them advantageous for surgical implantation. Thus, the ability to fabricate PGS fibers may be beneficial for tissue engineering applications by simultaneously providing contact guidance and superior mechanical properties. However, pure PGS is naturally difficult to electrospin. As stated by Yi et al. (*Macromol. Biosci.* 8(9): 803-806, 2008), "despite repeated efforts it was not possible to directly electrospin (and cure) nanofibers from either the polymerized PGS or the PGS prepolymer." There is no solvent for cross-linked PGS and PGS pre-polymer cannot form electrospun fibers on its own because it has a low molecular weight which precludes sufficient polymer chain entanglement to form fibers. PGS pre-polymer is also a viscous liquid at room temperature, causing any fibers formed to fuse rapidly after formation. Thus, there is a need in the art to develop methods of electrospinning PGS which allow stable PGS fibers and fibrous PGS scaffolds to be formed.

SUMMARY

Disclosed herein are methods of electrospinning PGS which overcome the limitations associated with the previous methods of electrospinning. The disclosed methods allow stable PGS fibers and fibrous PGS constructs, scaffolds and grafts to be formed. It is to be noted that inconsistencies exist in the nomenclature of PGS. In particular, previous publications which report electrospinning of PGS are in fact reporting the electrospinning of PGS prepolymer in a carrier polymer, not crosslinked PGS. Herein, the polymer before crosslinking is referred to as PGS prepolymer whereas the term "PGS" denotes crosslinked (cured) PGS.

In one example, a disclosed method includes generating PGS fibers, such as PGS micro- or nano-fibers by blending PGS prepolymer with a heat resistant natural or synthetic polymer carrier, including, but not limited to polyvinyl alcohol (PVA), polyhydroxybuytrate (PHB) or polyethylene terephthalate (PET), wherein the blend is electrospun into micro- or nano-fibers, and the PGS prepolymer is cross-linked into PGS with heat without using chemical cross-linkers. In these examples, standard electrospinning equipment and techniques are used and not core-shell electrospinning equipment and techniques. In some examples, the method further includes removing the heat-resistant "carrier polymer".

In one example, a disclosed method includes electrospinning PGS prepolymer and PVA, wherein electrospun PGS is cross-linked without using chemical cross-linkers; and the PVA is removed by washing with distilled water, thereby forming a PGS fibrous construct. In another example, a method of preparing a fibrous construct includes electrospinning PGS prepolymer and a natural carrier polymer, such as gelatin, wherein electrospun PGS is cross-linked with heat without using chemical cross-linkers, thereby forming a fibrous construct containing both PGS and the natural carrier, such as gelatin. Another example constructs a fibrous PGS construct by preparing an electrospinning precursor solution comprising blending PGS prepolymer with poly(lactic-co-glycolic acid) (PLGA) and a chemical cross-linker; electrospinning the prepared blend; and exposing the electrospun blend to an organic solvent to remove the PLGA. Also disclosed are compositions made therefrom, including fibrous constructs which can be used as scaffolds, such as tissue engineering scaffolds or cell-free implants, including for the replacement and/or repair of damaged native tissues.

The foregoing and other features and advantages of the disclosure will become more apparent from the following detailed description, which proceeds with reference to the accompanying figures.

BRIEF DESCRIPTION OF THE DRAWINGS

FIG. 2 is a pair of scanning electron microscope (SEM) images of gelatin (Type B) fibers before (top) and after (bottom) heat crosslinking 130° C. for 24 hours.

FIG. 3 is a pair of scanning electron microscope (SEM) images of PGS-gelatin (Type B) fibers with 25% PGS content, before (top) and after (bottom) heat crosslinking 130° C. for 24 hours.

FIG. 4 is a pair of scanning electron microscope (SEM) images of PGS-gelatin (Type B) fibers with 50% PGS content, before (top) and after (bottom) heat crosslinking 130° C. for 24 hours.

FIGS. 10A and 10B are digital images illustrating a sheet (FIG. 10A) or tube (FIG. 10B) formed by electrospinning onto a mandrel

FIGS. 15A-15L are a series of SEM images illustrating that complex shapes can be electrospun and retain structure as well as fiber morphology with the disclosed methods. FIGS. 15A-15C: Nerve guides with nylon templates (70, 130, 280 μm diameter, respectively) intact.

FIGS. 15D-15F: Nerve guides after removal of nylon templates by soaking guide in TFE. Most other materials dissolved, but PGS-gelatin resisted dissolution after brief curing. PGS-gelatin was also resistant to acetone, dimethylformamide, methanol, ethanol, and hexafluoro-2-propanol.

FIGS. 15G-15I: Zoom of FIGS. 15D-15F showing fibrous microstructure surrounding the microchannels. FIGS. 15J-15L: Compression cycle of hydrated PGS-gelatin nerve guide showing elastic recovery and open channels.

FIG. 17 is a series of SEM images illustrating that disclosed PGS-gelatin fibers are stable in an autoclave after sufficient curing.

FIG. 18 is a schematic illustrating an exemplary method of electrospinning tubular PGS implants using a blend of PGS and PGA containing chemical cross-linker

FIG. 20 is a series of digital images of a PGS graft implanted in rat abdominal aorta (left panel), an image of the middle of the graft (top right panel) and a microscope slide of the wall (bottom right panel).

FIG. 24 is a digital image (top panel) and series of SEM images of PGS-PVA fibers. FIG. 24 (top panel) provides a digital image of a sheet of 55 PGS-PVA electrospun with aluminum mandrel. FIG. 24 (bottom panel) provides a series of SEM images illustrating fiber morphology after electrospinning, crosslinking, and washing for 3 different blends of PGS-PVA.

FIG. 26 is a graph and pair of digital images illustrating the mechanical testing of the 55 PGS-PVA fibers showing a soft material with tunable tensile properties based on crosslinking.

FIGS. 27A-27C are digital images and FIGS. 27D and 27E are a pair of SEM images demonstrating the ability to fabricate fibrous tubes from PGS-PVA and PGS-PHB blends by electrospinning and heat crosslinking. FIG. 27A shows the electrospinning system. In FIG. 27B, fibers are shown to deposit unevenly on the unfixed end of the glass mandrel. FIG. 27C depicts a mandrel coated with PGS-PVA fibers after electrospinning. The annotations denote allocation of PGS fiber tubes for further processing. Three grafts are obtained from the fibers deposited on one glass mandrel. Dotted lines indicate the location where a small ring (1 to 2 mm thick) was taken for SEM imaging. FIGS. 27D and 27E are SEM images of PGS-PVA (FIG. 27D) and PGS-PHB (FIG. 27E) fibers.

DETAILED DESCRIPTION OF SEVERAL EMBODIMENTS

I. Overview of Several Embodiments

Figure 1:
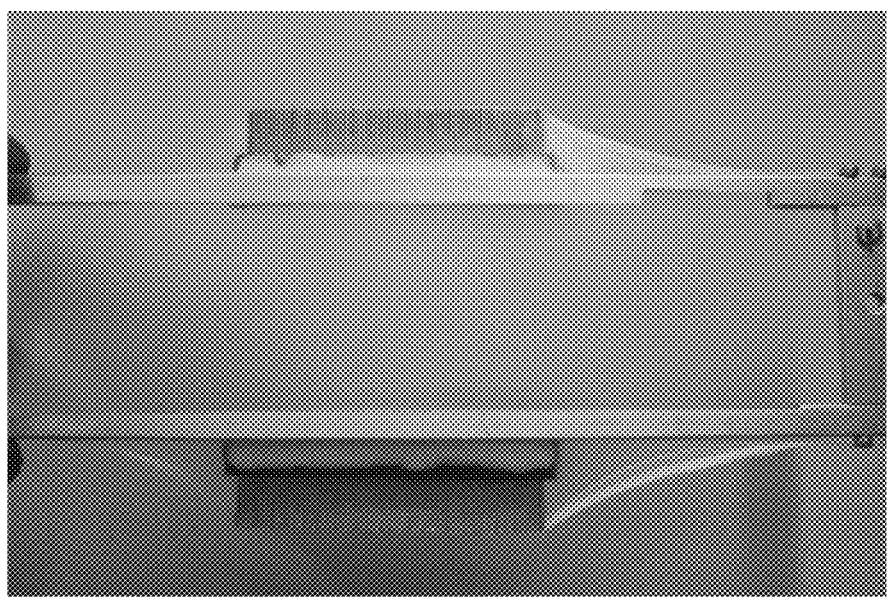
FIG. 1 is a digital image of an open collector used for collecting PGS-gelatin fibers illustrated in FIGS. 2-9.
Figure 5:
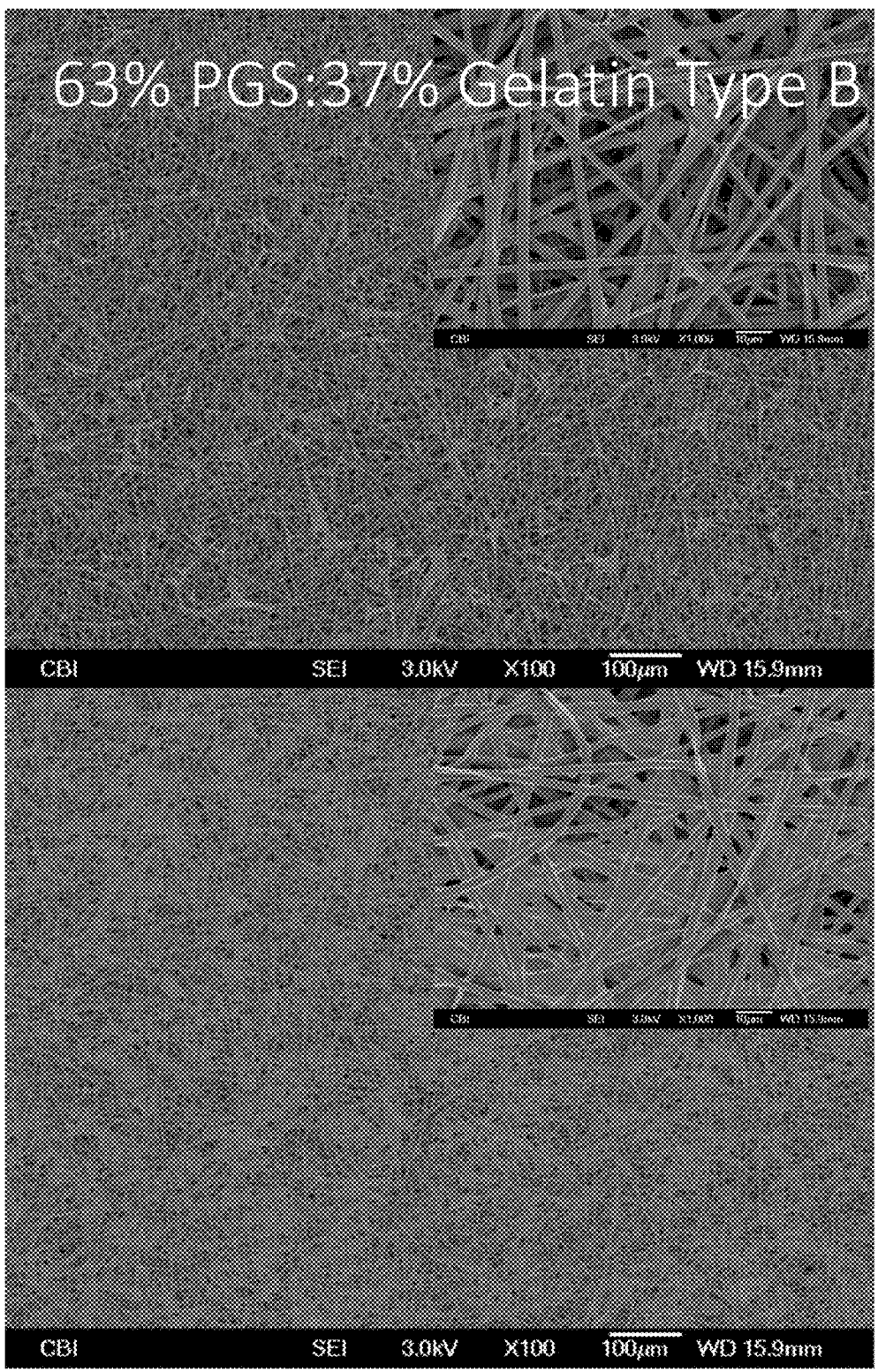
FIG. 5 is a pair of scanning electron microscope (SEM) images of PGS-gelatin (Type B) fibers with 63% PGS content, before (top) and after (bottom) heat crosslinking 130° C. for 24 hours.
Figure 6:
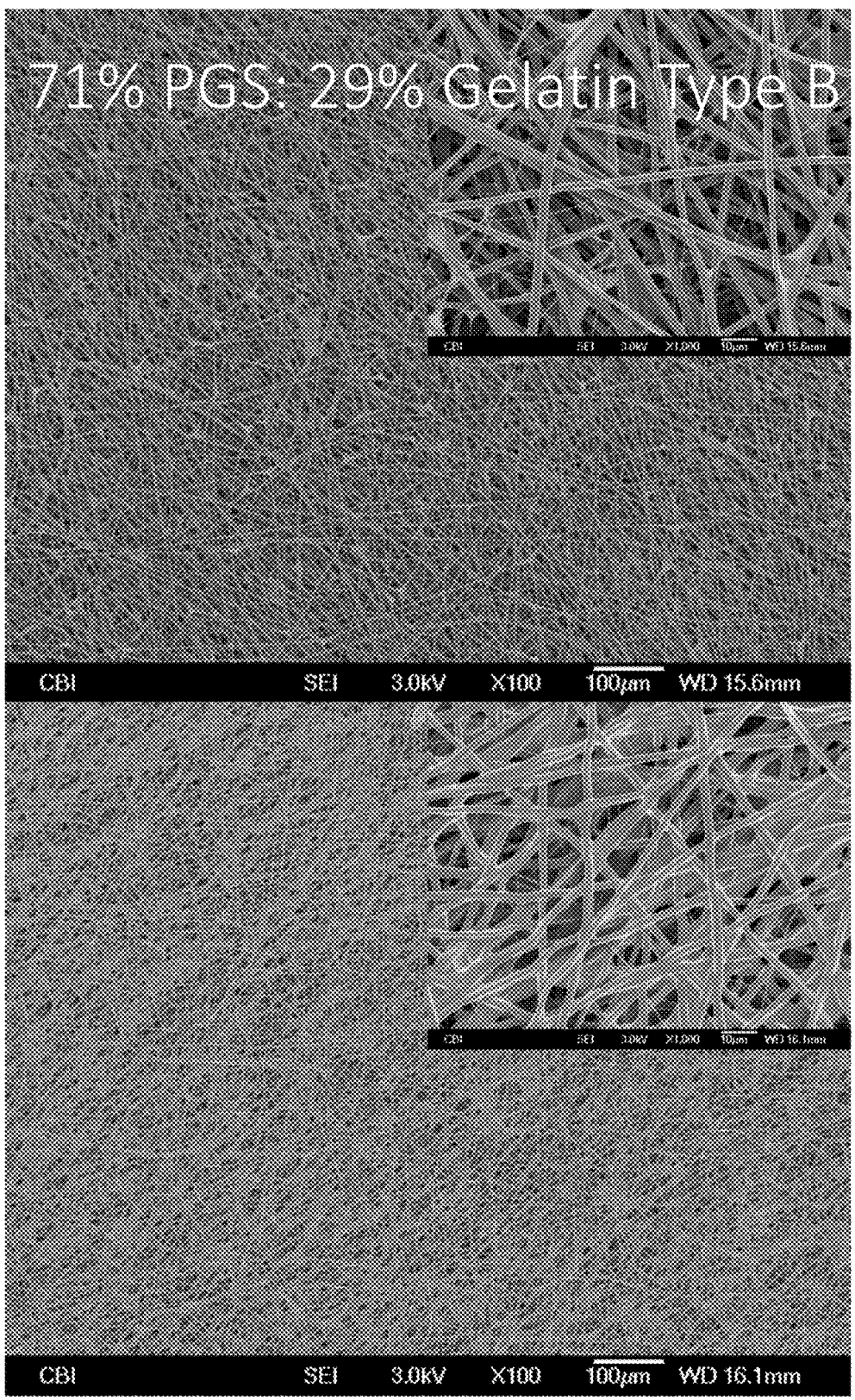
FIG. 6 is a pair of scanning electron microscope (SEM) images of PGS-gelatin (Type B) fibers with 71% PGS content, before (top) and after (bottom) heat crosslinking 130° C. for 24 hours.
Figure 7:
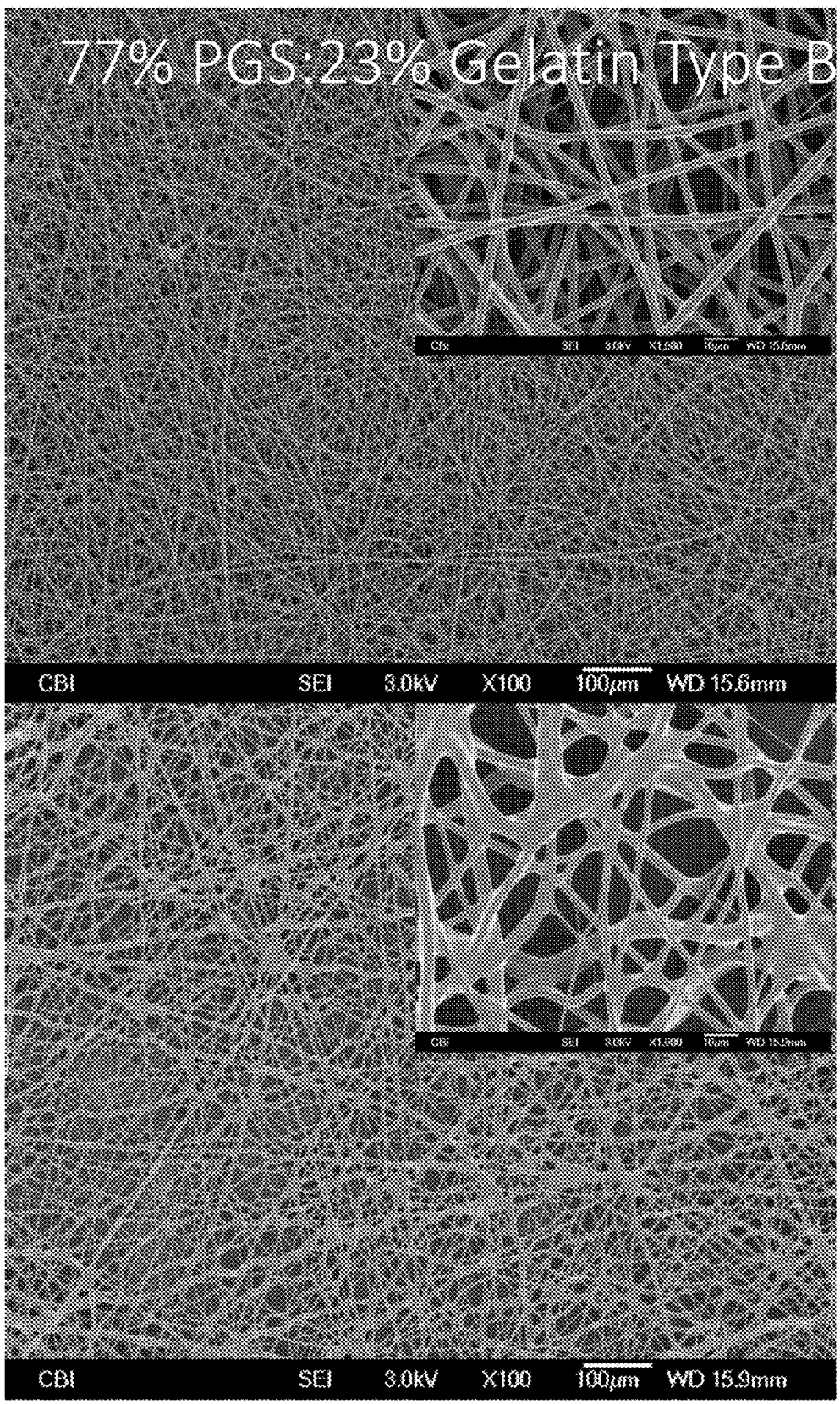
FIG. 7 is a pair of scanning electron microscope (SEM) images of PGS-gelatin (Type B) fibers with 77% PGS content, before (top) and after (bottom) heat crosslinking 130° C. for 24 hours.
Figure 8:
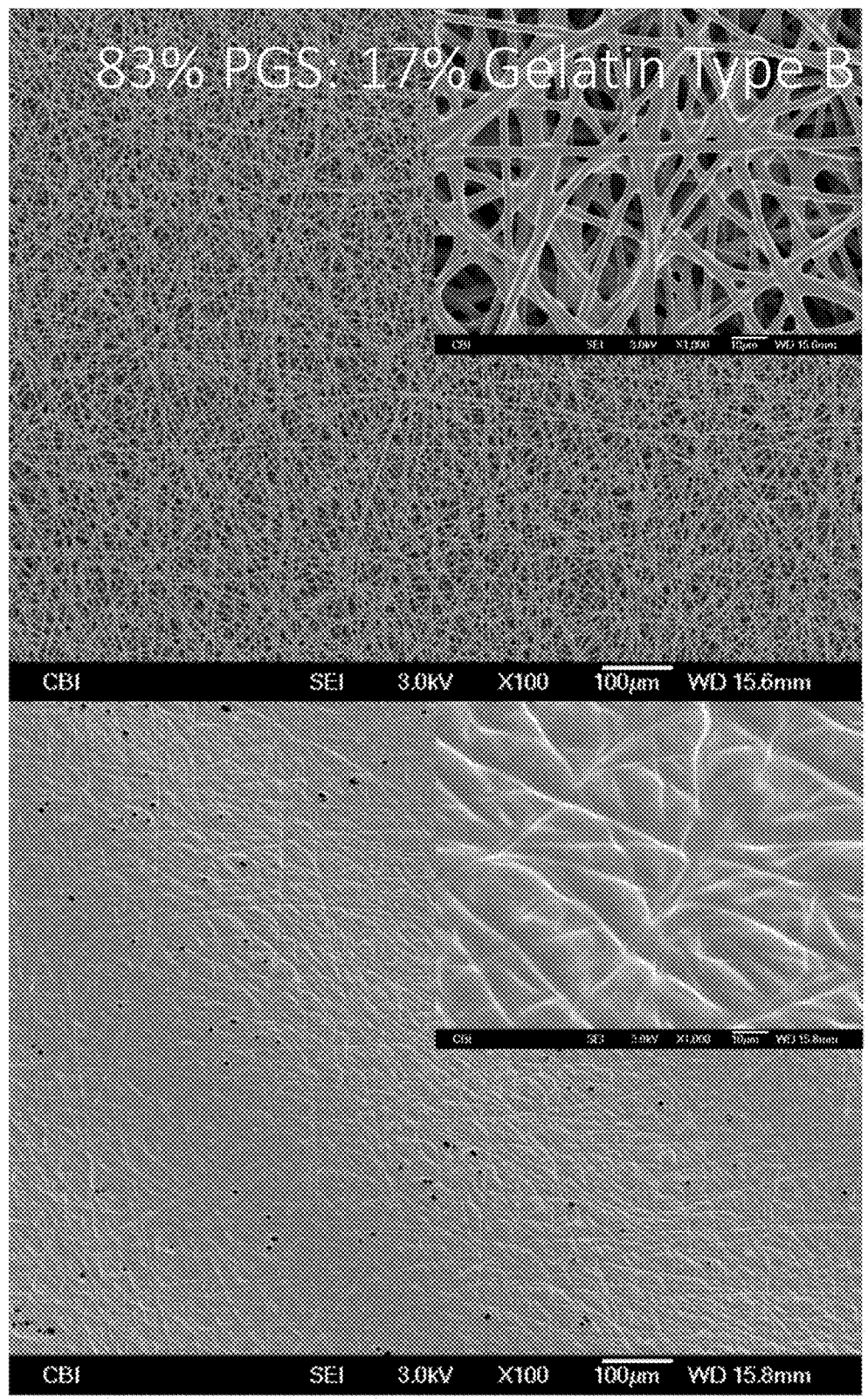
FIG. 8 is a pair of scanning electron microscope (SEM) images of PGS-gelatin (Type B) fibers with 83% PGS content, before (top) and after (bottom) heat crosslinking 130° C. for 24 hours.

Disclosed herein are methods of electrospinning PGS and compositions made therefrom, such as fibers and fibrous matrices/constructs which can be used as tissue engineering scaffolds or cell-free implants, including for the replacement and/or repair of damaged native tissues.

In some embodiments, the disclosed methods generate PGS fibers, such as PGS micro- or nano-fibers by blending PGS prepolymer with a heat resistant polymer ("carrier polymer"), including, but not limited to PVA, PHB or PET or a combination thereof, wherein the blend is electrospun into micro- or nano-fibers; and the PGS prepolymer is cross-linked into PGS with heat without using chemical cross-linkers. In some embodiments, standard electrospinning equipment and techniques are used and not core-shell electrospinning equipment and techniques. In other examples, core-shell electrospinning equipment and techniques are used either alone or in combination with standard electrospinning equipment and techniques.

In some embodiments, the method further includes removing the heat-resistant carrier polymer.

In some embodiments, the PGS prepolymer and a carrier polymer (such as PVA, PHB, PET or a combination thereof)

solution comprises PGS and a carrier polymer at a ratio of about 50:50; 45:55; 55:45; 40:60; or 60; 40, respectively.

In some embodiments of the method, heat curing comprises exposing electrospun PGS prepolymer and heat-resistant carrier polymer construct to between 70° C. and 200° C. temperature for between 2 weeks and 10 hours.

In some embodiments of the method, heat curing comprises exposing the electrospun PGS prepolymer and carrier polymer to 120° C. temperature for about 24 hours or 48 hours; or 150° C. for 24 hours; or 120° C. for 24 hours followed by 150° C. for 24 hours.

In some embodiments, a method of preparing a fibrous construct is disclosed comprising electrospinning a PGS prepolymer and gelatin solution, wherein the PGS prepolymer and gelatin is cross-linked with heat without using chemical cross-linkers, thereby preparing a fibrous construct.

In some embodiments, the method further comprises preparing a PGS and gelatin solution by combining PGS and gelatin with hexafluoroisopropanol (HFIP)-water prior to electrospinning.

In some embodiments, the PGS prepolymer and gelatin solution comprises PGS prepolymer and gelatin at a ratio of about 50:50.

In some embodiments of the method, heat curing comprises exposing the electrospun PGS prepolymer and gelatin to 130° C. temperature for about 24 hours.

In other embodiments, a method of preparing a fibrous construct is disclosed comprising preparing an electrospinning precursor solution comprising blending PGS prepolymer with poly(lactic-co-glycolic acid) (PLGA) and a chemical cross-linker; electrospinning the blended PGS prepolymer, PLGA and chemical cross-linker to form an electrospun PGS, PLGA, chemically cross-linked construct; and exposing the electrospun PGS, PLGA, chemically cross-linked construct to an organic solvent, thereby removing the PLGA and forming a PGS, chemically cross-linked construct.

In some embodiments of the method, the chemical cross-linker is lysine triisocyanate.

In some embodiments of the method, preparing an electrospinning precursor solution further comprises adding lithium bromide dissolved in tetrahydrofuran to the PGS prepolymer, PLGA and chemical cross-linker solution.

In some embodiments, a fibrous construct is disclosed which is formed by the disclosed methods.

In some embodiments, the fibrous construct further comprises a pharmaceutical agent.

In some embodiments, a scaffold made from a provided fibrous constructs is disclosed.

In some embodiments, a scaffold further comprises cells.

In some embodiments, a vascular graft is disclosed comprising a disclosed scaffold wherein the scaffold is tubular in shape and comprises an inner luminal surface and a thromboresistant agent coating the inner luminal surface of the scaffold, thereby forming a vascular graft.

In some embodiments, at least 95% of the vascular graft degrades within 90 days of implantation.

In some embodiments, the vascular graft is cell-free.

In some embodiments, the vascular graft is used for forming a blood vessel of less than 6 mm.

In some embodiments, the vascular graft is used for forming a blood vessel of less than 4 mm.

In some embodiments, the vascular graft is used as a coronary or a peripheral arterial graft.

In some embodiments, a method of fabricating a vascular graft is disclosed, comprising preparing a disclosed scaffold, wherein the scaffold is tubular in shape and comprises an inner luminal surface; and coating the inner luminal surface of the scaffold with a thromboresistant agent, thereby forming a vascular graft, in which at least 75% of the vascular graft degrades within 90 days of implantation in a subject.

In some embodiments, a composition that facilitates tissue regeneration by providing a structural frame is disclosed, comprising a disclosed scaffold and a thromboresistant agent coating the scaffold, thereby forming a composition that facilitates tissue regeneration in vivo by providing a structural frame.

II. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example." Although methods and materials similar or equivalent to those described herein can be used in the practice or testing of this disclosure, suitable methods and materials are described below. In addition, the materials, methods, and examples are illustrative only and not intended to be limiting.

In order to facilitate review of the various embodiments of this disclosure, the following explanations of specific terms are provided:

Anticoagulant: A substance that prevents the clotting of blood (coagulation). Anticoagulants are commonly administered to subjects to prevent or treat thrombosis. Generally, anticoagulants are administered to treat or prevent deep vein thrombosis, pulmonary embolism, myocardial infarction, stroke, and mechanical prosthetic heart valves. Various types of anticoagulants with different mechanisms of action are available including anticoagulants that inhibit the effect of vitamin K (such as coumadin) or thrombin directly (such as argatroban, lepirudin, bivalirudin, and ximelagatran) or that activate antithrombin II that in turn blocks thrombin from clotting blood (such as heparin and derivative substances thereof).

Biocompatible: A term describing something that can be substantially non-toxic in the in vivo environment of its intended use, and is not substantially rejected by the patient's physiological system (e.g., is nonantigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of subjects, will not cause a significantly adverse reaction or response. Furthermore, biocompatibility can be affected by other contaminants such as prions, surfactants, oligonucleotides, and other agents or contaminants. The term "biocompatible material" refers to a material that does not cause toxic or injurious effects on a tissue, organ, or graft.

Biodegradable polymer: A polymer that can be cleaved either enzymatically or hydrolytically to break it down sufficiently so as to allow the body to absorb or clear it away. A biodegradable vascular graft is a graft in which at least a significant portion (such as at least 50%) of the graft degrades within one year of implantation.

Cell-free graft: A graft which does not contain cells, such as, endothelial or smooth muscle cells at the time of implantation.

Coat: As used herein "coating", "coatings", "coated" and "coat" are forms of the same term defining material and process for making a material where a first substance or substrate surface is at least partially covered or associated with a second substance. Both the first and second substance are not required to be different. Further, when a surface is "coated" as used herein, the coating may be effectuated by any chemical or mechanical bond or force, including linking agents. The "coating" need not be complete or cover the entire surface of the first substance to be "coated". The "coating" may be complete as well (e.g., approximately covering the entire first substance). There can be multiple coatings and multiple substances within each coating. The coating may vary in thickness or the coating thickness may be substantially uniform. Coatings contemplated in accordance with the present disclosure include, but not limited to medicated coatings, drug-eluting coatings, drugs or other compounds, pharmaceutically acceptable carriers and combinations thereof, or any other organic, inorganic or organic/inorganic hybrid materials. In an example, the coating is a thromboresistant coating which has anticoagulant properties, such as heparin.

Cross-link or chemical cross-linker: A cross-link is a bond, such as a covalent or ionic bond, that links one polymer chain to another. "Polymer chains" can refer to synthetic polymers or natural polymers (such as proteins). Mixing of an unpolymerized or partially polymerized resin with specific chemicals called crosslinking reagents results in a chemical reaction that forms cross-links. The resulting modification of mechanical properties depends strongly on the cross-link density. Low cross-link densities decrease the viscosities of polymer melts. Intermediate cross-link densities transform gummy polymers into materials that have elastomeric properties and potentially high strengths. Very high cross-link densities can cause materials to become very rigid or glassy, such as phenol-formaldehyde materials. In one example, a chemical cross-linker is lysine triisocyanate.

Electroaerosoling: A process in which droplets are formed from a solution or melt by streaming an electrically charged polymer solution or melt through an orifice.

Electroprocessing: A process which includes any means of using an electrical field for depositing a material on a target.

Electrospinning: A process in which fibers are formed from a solution or melt by streaming an electrically charged solution or melt through an orifice.

Gelatin: A rapidly-degrading biocompatible material derived from collagen. Gelatin acts as a carrier for PGS to permit fiber formation by increasing fiber entanglement. Additionally, increased gelatin improves the morphology of fibers by reducing fiber fusion during electrospinning and heat curing. Gelatin may also have benefits for promoting cell adhesion and does not need to be removed like other carrier polymers. The disclosed methods herein utilize gelatin as a natural carrier polymer.

Heat-resistant carrier polymer: A polymer with sufficiently high glass transition temperatures and/or melting temperatures such that they remain solid or semi-solid at temperatures of 100 to 150° C., such as PVA, PHB, PET, polydioxanone (PDO), or poly(lactic acid) (PLA).

Pre-polymer: A monomer or system of monomers that have been reacted to an intermediate molecular weight state. This material is capable of further polymerization by reactive groups to a fully cured high molecular weight state. As such, mixtures of reactive polymers with un-reacted monomers may also be referred to as pre-polymers. The term "pre-polymer" and "polymer precursor" may be interchanged. In some examples, a pre-PGS polymer is used in the disclosed methods to construct the disclosed PGS fibers.

Poly(caprolactone)(PCL): A biodegradable polyester with a low melting point of around 60° C. and a glass transition temperature of about −60° C. PCL is prepared by ring opening polymerization of ε-caprolactone using a catalyst such as stannous octoate. PCL is degraded by hydrolysis of its ester linkages in physiological conditions (such as in the human body) and can be used as an implantable biomaterial.

Polyethylene terephthalate (PET): A thermoplastic polymer resin of the polyester family used in synthetic fibers. PET is formed with polymerized units of the monomer ethylene terephthalate, with repeating $C_{10}H_8O_4$ units. Clinical grade PET is an FDA approved material for vascular grafts. In some examples, PET is used as a carrier polymer in the disclosed methods and is blended with PGS.

Poly(glycerol sebacate) (PGS): An elastomeric biodegradable polyester. In some examples, PGS is electrospun with gelatin to form fibrous constructs. In some examples, PGS prepolymer is blended with a synthetic polymer such as polyvinyl alcohol (PVA), polyhydroxybuytrate (PHB) or polyethylene terephthalate (PET). In some examples, PGS prepolymer is blended with poly(lactic-co-glycolic acid) (PLGA) and a chemical cross-linker, then electrospun as a blended material. The PLGA is removed with organic solvent to leave only PGS fibers. In some examples, PGS prepolymer is blended with gelatin.

Polyhydroxybuytrate (PHB): A polyhydroxyalkanoate (PHA), a polymer belonging to the polyesters class that is of interest as bio-derived and biodegradable plastics. PHB has a melting point 175° C., glass transition temperature 2° C. and a tensile strength 40 MPa, close to that of polypropylene. In some examples, PHB is used as a carrier polymer in the disclosed methods and is blended with PGS prepolymer prior to electrospinning and crosslinking.

Polyvinyl alcohol (PVA): PVA is a synthetic polymer produced by partial or full hydrolysis of polyvinyl acetate with solubility and crystallinity dependent on the degree hydrolysis and polymerization. PVA is nontoxic, noncarcinogenic, and approved for food contact by FDA. PVA hydrogels have been implanted for a variety of applications including tissue adhesion barriers, nerve guides, and cartilage replacement. PVA is water soluble and retains GRAS (generally recognized as safe) status with the FDA as a food additive. In some examples, PVA is used as a carrier polymer in the disclosed methods and is blended with PGS. PVA is suitable for the outlined applications due to its high solubility in HFIP for electrospinning and in water for carrier removal.

Scaffold: A structural support facilitating cell infiltration and attachment in order to guide vessel growth. As disclosed herein, a biodegradable scaffold can be used to form a vascular graft. In some examples, a biodegradable scaffold includes electrospun PGS-gelatin or electrospun, chemically cross-linked PGS.

Subject: Living multi-cellular vertebrate organisms, a category that includes human and non-human mammals (such as laboratory or veterinary subjects). In an example, a subject is a human. In an additional example, a subject is selected that is in need of an implant for damaged or defective artery.

Vascular graft: A tubular member which acts as an artificial vessel. A vascular graft can include a single material, a blend of materials, a weave, a laminate or a composite of two or more materials.

III. Methods of Fabrication and Compositions Therefrom

PGS is widely used for developing soft tissue implants because it degrades rapidly and has biocompatibility advantages over other degradable polyesters. Electrospinning fabrication improves the commercialization potential of PGS implants by dramatically improving mechanical strength and reducing fabrication cost and time. However, prior to the presently disclosed methods, PGS was difficult to electrospin. There was no solvent for cross-linked PGS, and PGS prepolymer cannot form electrospun fibers on its own because it has a low molecular weight which precludes sufficient polymer chain entanglement to form fibers. PGS prepolymer is also a viscous liquid at room temperature, causing any fibers formed to fuse rapidly after formation. Disclosed herein are methods of electrospinning PGS which overcome these previous limitations. Although electrospinning is the preferred form of electroprocessing the disclosed compositions, it is contemplated that other/additional types of "electroprocessing" could be employed. Electroprocessing includes all methods of electrospinning, electrospraying, electroaerosoling, and electrosputtering of materials, combinations of two or more such methods, and any other method wherein materials are streamed, sprayed, sputtered or dripped across an electric field and toward a target. The term electroprocessing is not limited to the specific examples set forth herein, and it includes any means of using an electrical field for depositing a material on a target.

i. PGS:PVA, PHB or PET

In some embodiments, the disclosed methods generate PGS fibers, such as PGS micro- or nano-fibers by blending PGS pre-polymer with a carrier polymer such as a heat-resistant carrier polymer, including, but not limited to PVA, PHB, PET, PDO, PLA or a combination thereof, wherein electrospinning is used to spin the blend into micro- or nano-fibers and cross-linking the PGS prepolymer into PGS is accomplished with heat. This method does not use chemical cross-linkers. In these embodiments, standard electrospinning equipment and techniques are used and not core-shell electrospinning equipment and techniques. In some embodiments, the method further includes removing the heat-resistant "carrier polymer", such as removing PVA, PHB, PET, PDO, or PLA. These methods generate PGS fibers with at least the following unique set of advantages: (1) PGS fibers are cross-linked, thus they retain the desired profile of biocompatibility and strength; (2) cross-linking is achieved with heat, minimizing residual toxicity compared with other methods; and (3) fabrication requires standard electrospinning equipment and does not require equipment or processes needed for core-shell electrospinning, thus it is must more cost and time efficient. Additionally, prior to the present disclosure, no previously reported methods were able to generate electrospun PGS fibers which were cross-linked with the desired profile of biocompatibility and strength by using heat and standard electrospinning equipment. Instead, previous methods used core-shell electrospinning equipment or techniques (with a heat-resistant carrier) or other methods of crosslinking (such as with light) or no crosslinking to produce such fibers. Moreover, prior to the present disclosure no one had demonstrated or suggested removing a blended carrier polymer from fibers made from a blend of PGS and a carrier polymer.

In some embodiments, the method includes electrospinning PGS pre-polymer with a heat-resistant carrier polymer, such as PVA, PHB or PET or a combination thereof. In some embodiments, a method of preparing fibrous constructs comprising co-electrospinning PGS and one or more heat-resistant polymers, including, but not limited to PVA, PHB or PET, followed by varied heat curing. PGS blend solutions are prepared and electrospun onto a variety of collectors, such as a mandrel. In some examples, the solution includes between 5% and 95% PGS pre-polymer and 95% to 5% heat-resistant carrier polymer, such as 25% to 75% PGS pre-polymer and 75% to 25% heat-resistant carrier polymer, including 35% to 65% PGS pre-polymer and 65% to 35% heat-resistant carrier polymer, 30% to 70% PGS pre-polymer and 70% to 30% heat-resistant carrier polymer, 45% to 55% PGS pre-polymer and 55% to 45% heat-resistant carrier polymer, or 50% PGS pre-polymer and 50% heat-resistant carrier polymer, or 40% to 60% PGS pre-polymer and 60% to 40% heat-resistant carrier polymer including 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, or 95% PGS pre-polymer and 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52,%, 51%, 50%, 49%, 48%, 47%, 46%, 45%, 44%, 43%, 42%, 41%, 40%, 39%, 38%, 27%, 36%, 35%, 24%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% heat resistant polymer, such as PVA, PHB or PET or a combination thereof. In some examples, a heat resistant carrier polymer is present at equal to or less than 90% of the solution.

Standard electrospinning principles and techniques can be used with preparing PGS pre-polymer blend solutions. It is contemplated that any solvent can be used that allows delivery of the material or substance to the orifice, tip of a syringe, or other site from which the material will be electroprocessed. The solvent may be used for dissolving or suspending the material or the substance to be electroprocessed. Solvents useful for dissolving or suspending a material or a substance depend on the material or substance. Electrospinning techniques often require more specific solvent conditions, such as urea, monochloroacetic acid, isopropanol, 2,2,2-trifluoroethanol, 1,1,1,3,3,3-hexafluoro-2-propanol (also known as hexafluoroisopropanol or HFIP), water or combinations thereof. Urea, monochloroacetic acid, water, 2,2,2-trifluoroethanol, HFIP, or combinations thereof may be utilized. Other lower order alcohols, especially halogenated alcohols, may be used. Other solvents that may be used or combined with other solvents in electroprocessing include acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone, tetrahydrofuran (THF), trichloromethane (chloroform), dichloromethane (DCM).

In this embodiment, chemical crosslinkers are not used with the PGS pre-polymer blend solutions. Rather, heat crosslinking is used. For example, to achieve observable crosslinking (solvent resistance and increased mechanical strength), constructs are placed in a vacuum oven at temperatures of between 37° C. and 200° C. for at least 4 hours, such as between 110° C. and 140° C., including 40° C., 50° C., 60° C., 70° C., 80° C., 90° C., 100° C., 110° C., 115° C., 120° C., 125° C. 130° C., 135° C., 140° C., or 150° C. for at least 4 hours, such as between 4 to 48 hours, 12 to 24 hours, 24 to 48 hours at temperatures including 4 hours, 8 hours, 12 hours, 24 hours, 30 hours, 36 hours, 42 hours, 48 hours, 3 days, 4 days, 5 days, 6 days, 7 days, 8 days, 9 days, 10 days, 11 days, 12 days, 13 days or 14 days. It is contemplated that a lower temperature will take a longer period of time for sufficient crosslinking. For example, use of a temperature of 70° C. may take up to 14 days for crosslinking whereas a temperature of 200° C. may take up to 10 hours. Variation of these parameters, not limited to this range or duration, should permit control of the degree of crosslinking. In some examples, PGS pre-polymer blend solutions are prepared, electrospun onto a variety of collectors, such as a mandrel, and then crosslinked with heat, such as by heating at 120° C. for 24 hours. Further, varying the ratio of PGS to heat-resistant carrier polymer, such as PVA, PHB or PET alters the integrity of fibers/fiber fusion. As mentioned, one difficulty of electrospinning PGS is to prevent fiber fusion and film formation. However, slight fusion of fibers can be very useful for constructing 3-dimensional constructs where many other electrospun layers would delaminate. Thus, the inventors demonstrate herein the ability to form a range of fiber morphologies ranging from highly-defined fibers to fused porous mats by altering the PGS to heat-resistant carrier polymer ratio. In some examples, the heat-resistant carrier polymer is removed.

ii. PGS:Gelatin

In some embodiments, the method includes electrospinning PGS with gelatin. In some embodiments, a method of preparing fibrous constructs of unmodified PGS-gelatin is disclosed comprising co-electrospinning PGS and gelatin followed by varied heat curing. PGS-gelatin blend solutions are prepared and electrospun onto a variety of collectors, such as a mandrel. In some embodiments, the PGS-gelatin blend solutions are prepared in hexafluoroisopropanol (HFIP)-water (31:1 ratio of HFIP:water) and then electrospun. In some examples, the PGS-gelatin blend solutions are prepared in hexafluoroisopropanol (HFIP) alone and in the presence of rocking while at 37° C. until in solution (for example, for 8 to 24 hours). In some examples, the solution includes between 5% and 95% PGS and 95% to 5% gelatin, such as 25% to 75% PGS and 75% to 25% gelatin, including 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, or 95% PGS and 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 24%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% gelatin.

Standard electrospinning principles and techniques can be used with PGS-gelatin solutions. It is contemplated that any solvent can be used that allows delivery of the material or substance to the orifice, tip of a syringe, or other site from which the material will be electroprocessed. The solvent may be used for dissolving or suspending the material or the substance to be electroprocessed. Solvents useful for dissolving or suspending a material or a substance depend on the material or substance. Electrospinning techniques often require more specific solvent conditions, such as urea, monochloroacetic acid, isopropanol, 2,2,2-trifluoroethanol, 1,1,1,3,3,3-hexafluoro-2-propanol (also known as hexafluoroisopropanol or HFIP), water or combinations thereof. Other lower order alcohols, especially halogenated alcohols, may be used. Other solvents that may be used or combined with other solvents in electroprocessing natural matrix materials include acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone.

In one desirable embodiment, PGS and gelatin are co-electrospun in HFIP. Without being bound by a particular theory, it is believed that gelatin acts as a carrier for PGS to permit fiber formation by increasing fiber entanglement. Additionally, increased gelatin is believed to improve the morphology of fibers by reducing fiber fusion during electrospinning and heat curing. Gelatin can also have benefits for promoting cell adhesion and does not need to be removed like other carrier polymers. Conversely, PGS increases fiber fusion and is beneficial for reducing delamination of multi-layered constructs. PGS also adds elastomeric properties to the construct, which can be tailored based on curing conditions. Varying the ratio of these two components can be used to fit the needs of the application.

In this embodiment, chemical crosslinkers are not used with the PGS or gelatin. Rather, heat crosslinking is used. For example, to achieve observable crosslinking (solvent resistance and increased mechanical strength), constructs are placed in a vacuum oven at temperatures of between 100 and 150° C. for at least 24 hours, such as between 110 and 140° C., including 110° C., 115° C., 120° C., 125° C. 130° C., 135° C., 140° C., or 150° C. for at least 24 hours, such as between 24 to 48 hours, including 24 hours, 30 hours, 36 hours, 42 hours, or 48 hours. Variation of these parameters, not limited to this range or duration, should permit control of the degree of crosslinking. In some examples, PGS-gelatin blend solutions are prepared, electrospun onto a variety of collectors, such as a mandrel, and then crosslinked with heat, such as by heating at 130° C. for 24 hours. Electrospun constructs with certain chemical crosslinkers may cause reduced cytocompatibility. For example, photo-crosslinked-acrylated PGS increased inflammation with increasing acrylation. Additionally, in some embodiments, this method is performed in the absence of a synthetic carrier polymer, such as poly(lactic acid) (PLA), polycaprolactone (PCL) or poly(glycolic acid) (PGA), and the copolymer poly(lactide-co-glycolide) (PLGA). Co-electrospinning with such polymers can alter the elastomeric properties while increasing degradation time and acidity. Contrarily, gelatin is rapidly degraded by enzymes in the body and may actually aid cell adhesion. However, its mechanical properties vary greatly between hydrated and dehydrated states and is much weaker than other polyester carrier polymers such as PLGA and PCL. The ability to use this method with electrospinning is also surprising because prepolymer PGS was known to fuse into a film. It is contemplated that gelatin prevents the PGS from losing shape during heat curing. It is disclosed that a range of temperatures including low-heat can be used to crosslink a prepolymer PGS. High temperature, such as between 100-150° C., can be used for curing to achieve constructs with mechanical properties similar to tissue. Low temperatures (below 100° C.) are used in constructs with other biomaterials (e.g., PCL 60° C. mp) with low melting temperature. Low temperatures, (such as below 37° C.) are beneficial for minimizing protein denaturation, but involve substantial additional time for curing to achieve a relevant amount of crosslinking. Low heat may permit spinning of cells into construct which is desirable since electrospun constructs can be difficult for cells to penetrate. Further, varying the ratio of PGS to gelatin alters the integrity of fibers/fiber fusion. As mentioned, one difficulty of electrospinning PGS is to prevent fiber fusion and film formation. However, slight fusion of fibers can be very useful for constructing 3-dimensional constructs where many other electrospun layers would delaminate. Thus, the inventors demonstrate herein the ability to form a range of fiber morphologies ranging from highly-defined fibers to fused porous mats by altering the PGS to gelatin ratio. The disclosed methods overcome the difficulty of electrospinning PGS to form fibrous constructs as well as delamination of multi-layered fibrous constructs. In some examples, PGS is used as an additive in other electrospun polymers to reduce delamination.

iii. PGS: PLGA

Also disclosed are methods of electrospinning PGS, in which PGS prepolymer is blended with PLGA and a chemical cross-linker, then electrospun as a blended material. The PLGA can either be left within the blend or removed with organic solvent to leave only PGS fibers. For example, this method is used to produce fibrous constructs comprised of either PGS or PGS and PLGA. In some examples, fibrous constructs comprised of either PGS or PGS and PLGA are used to form implants that bear mechanical loads and/or must be sutured in place (e.g., arterial vascular grafts). In some examples, fibrous constructs comprised of either PGS or PGS and PLGA are used for skin and muscle healing applications, since such implants will bear load and stretch when in situ.

In some embodiments, the method includes producing fibrous constructs from PGS by (1) blending PGS prepolymer with poly(lactic-co-glycolic acid) (PLGA) and a chemical cross-linker, such as lysine triisocyanate, hexamethylene diisocyanate, and any other di-, tri-, or polyisocyanates, (2) electrospinning, and (3) dissolving the PLGA with organic solvent. In some embodiments, the electrospinning precursor solution contains PGS prepolymer, PLGA, lysine triisocyanate, and lithium bromide dissolved in tetrahydrofuran.

TABLE 1A

| Name | Units | Max | Min | Typical |
|---|---|---|---|---|
| PGS prepolymer:PLGA mass ratio | % | 90 | 1 | 70 |
|  | Ratio | 9to1 | 1 | 7to3 |
| Total polymer concentration | % | 30 | 2.5 | 18 |
|  | g/mL | 0.3 | 0.025 | 0.18 |
| Organic solvent | % | 95 | 70 | 82 |
|  | g/mL | 0.95 | 0.7 | 0.82 |
| Lysine triisocyanate chemical cross-linker | % | 2 | 0 | 1.15 |
|  | mg/mL | 20 | 0 | 11.5 |
| Lithium Bromide | mM (millimolar) | 1000 | 10 | 300 |
|  | g/L | 86.84 | 0.8684 | 26.052 |
|  | mg/mL | 86.84 | 0.8684 | 26.052 |

TABLE 1B

|  | Processing step | Max (min) | Reason | Min (min) | Reason | Typical (hrs) | Reason |
|---|---|---|---|---|---|---|---|
| Time of exposure to lysine triisocyanate | Mixing precursor solution and electrospinning it | 180 | Reaction is slow, but by 180 min the solution will have cross-linked into an unspinnable gel | 0 | Electrospinning can proceed without cross-linker, so low exposure times do not affect the ability to electrospin | 0 | Electrospinning is best started immediately after cross-linker is added |
|  | Drying electrospun fibers under vacuum at room temperature | infinite | Vast majority of triisocyanate will be reacted within 7 days, so the fibers are stable by then | 180 | Lysine triisocyanate needs a minimum amount of time to react before processing can continue | 48 | Yields best mechanical properties |

PGS prepolymer is blended with PLGA in the electrospinning precursor solution because PLGA easily forms electrospun fibers. PLGA incorporates PGS prepolymer into its fibers as they form, yielding blended PGS prepolymer-PLGA fibers. The chemical cross-linker lysine triisocyanate is also mixed into the electrospinning precursor solution to chemically cross-link the PGS prepolymer into PGS. Lithium Bromide is also added to improve the electrical conductivity of the solution, which further promotes fiber formation. Standard electrospinning techniques are used to electrospin the precursor solution into microfibers. PGS prepolymer cross-links into PGS via lysine triisocyanate over the course of the treatment, such as over the course of 48 hours. PLGA is removed by washing the construct in organic solvents. Unreacted lysine triisocyanate residues are quenched by soaking in water, then removed by washing in organic solvents. Lithium bromide is also removed with water and organic solvents. The result is a tough, elastic construct containing only PGS. Alternatively, PLGA is left within the construct forming a strong, stiff construct containing both PGS and PLGA.

The disclosed method overcomes the difficulty of electrospinning PGS to form fibrous constructs. Further it produces PGS constructs with mechanical strength superior to existing PGS constructs. For example, disclosed electrospun PGS constructs comprise a tensile elastic modulus greater than 0.09 MPa, such as between 0.1 and 2 MPa, including 0.1, 0.2, 0.3, 0.4, 0.5, 0.6, 0.7, 0.8, 0.9, 1.0, 1.1, 1.2, 1.25, 1.3, 1.4, and 1.5 MPa. Disclosed electrospun PGS constructs comprise a ultimate tensile stress greater than 0.075 MPa, such as between 0.075 and 2 MPa or between 1 and 1.5 MPa, including 0.075, 0.08, 0.09, 0.1, 0.2, 0.3, 0.4, 0.5, 0.6, 0.7, 0.8, 0.9, 1.0, 1.1, 1.2, 1.25, 1.3, 1.4, and 1.5 MPa. Average fiber diameter is 5 μm for the typical construct, but can be tuned from 100 nm to 50 μm by adjusting the precursor solution composition and electrospinning parameters. Thickness of the fibrous sheet is typically 150 μm for tubular vascular grafts, but can be tuned to any thickness by altering the duration of collecting electrospun fibers. Fabrication of a disclosed fiber, construct and/or graft is also faster (22% reduction in total fabrication time) and simpler (49% reduction in time requiring skilled labor (e.g., can be done by automation) than solvent casting/salt leaching, the most common fabrication method for porous PGS constructs.

iv. Methods of Fabricating a Graft with any of the Disclosed PGS Compositions

In some particular examples, methods of fabricating a graft, such as a vascular graft are provided. In some embodiments, a method of fabricating a graft, such as a vascular graft, which is biodegradable and/or biocompatible comprises electrospinning PGS with gelatin, PGS pre-polymer with PLGA, PGS pre-polymer with PVA, PET or PHB, or crosslinking PGS as disclosed herein and generating a graft with the desired shape and properties. In some examples, the graft is shaped based upon the shape of the structure, such as a blood vessel, the resulting vascular graft is replacing. In some examples, a PGS tube is formed.

In some examples, the fabricated scaffold or graft comprises pores of about 1 μm to about 500 μm, from about 10 μm to about 300 μm, about 20 μm to about 300 μm, about 1 μm to about 10 μm, about 3 μm to about 7 μm, such as 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 30 μm, 40 μm, 50 μm, 60 μm, 70 μm, 80 μm, 90 μm, 100 μm, 150 μm, 200 μm, 250 μm, 300 μm, 350 μm, 400 μm, 450 μm, or 500 μm. In some examples, pores are about 20 μm to about 30 μm, including about 20 μm, 21 μm, 22 μm, 23 μm, 24 μm, 25 μm, 26 μm, 27 μm, 28 μm, 29 μm, and 30 μm. In some examples, the scaffold or graft is fabricated to include uniformly distributed pores. In some examples, the scaffold or graft is fabricated to include non-uniformly distributed pores. In some examples, the scaffold or graft is fabricated to not include any pores.

In some examples, the scaffold or graft is fabricated to include at least 75% pore interconnectivity, such as about 80% to about 90%, about 90% to about 98%, including 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% interconnectivity.

The various dimensions of a disclosed scaffold or vascular graft may vary according to the desired use. In some examples, the method of fabrication is performed to generate a vascular graft with an inner diameter which matches that of the host vessel to be replaced. In some examples, the inner diameter is between about 1 mm to 5 mm. In some examples, a disclosed vascular graft has an inner diameter of between about 700 μm to about 5000 μm, such as about 710 μm to about 4000 μm, such as about 720 μm to about 3000 μm, such as about 1000 μm to about 5000 μm, including 710 μm, 711 μm, 712 μm, 713 μm, 714 μm, 715 μm, 716 μm, 717 μm, 718 μm, 719 μm, 720 μm, 721 μm, 722 μm, 723 μm, 724 μm, 725 μm, 726 μm, 727 μm, 728 μm, 729 μm, 730 μm, 731 μm, 732 μm, 733 μm, 734 μm, 735 μm, 736 μm, 737 μm, 738 μm, 739 μm, 740 μm, 741 μm, 742 μm, 743 μm, 744 μm, 745 μm, 746 μm, 747 μm, 748 μm, 749 μm, 750 μm, 800 μm, 850 μm, 900 μm, 950 μm, 1000 μm, 2000 μm, 3000 μm, 4000 μm or 5000 μm. In some examples, the inner diameter of a disclosed vascular graft is fabricated to be about 720 μm. In some examples, the inner diameter of a disclosed vascular graft is fabricated to be about 1000 μm. In some examples, the inner diameter of a disclosed vascular graft is fabricated to be about 1200 μm. In some examples, the inner diameter of a disclosed vascular graft is fabricated to be about 2000 μm. In some examples, the inner diameter of a disclosed vascular graft is fabricated to be about 3000 μm.

In some examples, the method of fabrication is performed to generate a vascular graft with a wall thickness which matches that of the host vessel to be replaced. However, it is contemplated the graft wall can be fabricated with a thicker or thinner wall than that which is being replaced, if desired. In some examples, a disclosed vascular graft is fabricated to have a wall thickness between about 100 μm and about 500 such as about 150 μm and about 450 including about 200 μm and about 400 μm, such as about 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm or 500 μm. In some examples, a disclosed vascular graft is fabricated to have a wall thickness between about 270 μm and about 300 such as about 285 μm and about 295 including 270 μm, 271 μm, 272 μm, 273 μm, 274 μm, 275 μm, 276 μm, 277 μm, 278 μm, 279 μm, 280 μm, 281 μm, 282 μm, 283 μm, 284 μm, 285 μm, 286 μm, 287 μm, 288 μm, 289 μm, 290 μm, 291 μm, 292 μm, 293 μm, 294 μm, 295 μm, 296 μm, 297 μm, 298 μm, 299 μm or 300 μm. In some examples, the wall thickness is about 290 μm.

In some examples, the method of fabrication are performed to generate a scaffold or vascular graft that at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of such vascular graft degrades within one year, such as within 1 to 10 months, including within 1 month, 2 months, 3 months, 4 months, 5 months, 6 months, 7 months, 8 months, 9 months, 10 months, 11 months, or 12 months of implantation.

In some examples, the method of fabrication includes generating a cell-free scaffold or graft, such as a cell-free vascular graft, in which the graft does not include any living cells, such as smooth muscle cells, endothelial cells, stem cells, or progenitor cells.

In further examples, the disclosed methods of fabrication include impregnating or coating a surface of a generated fiber, scaffold or graft with a biocompatible and/or biodegradable material. It is contemplated that one of ordinary skill in the art can determine with but limited experimentation, which substrates are suitable for a particular application. In some examples, the inner luminal surface of the biodegradable scaffold is coated with a biocompatible and/or biodegradable material. It is contemplated that such coating may be complete or partial. In some examples, the outer (abluminal) surface of the biodegradable scaffold is coated with a biocompatible and/or biodegradable material. It is contemplated that such coating may be complete or partial.

In some examples, the disclosed methods of fabrication include impregnating or coating a surface of a generated fiber, scaffold or graft with one or more, such as two, three, four, five etc. suitable pharmaceutical agents. It is contemplated that suitable pharmaceutical agents can be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Pharmaceutical agents include any therapeutic molecule including, without limitation, any pharmaceutical substance or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present disclosure.

In some examples, the inner luminal surface of a biodegradable scaffold is coated partially or completely with a thromboresistant agent, such as heparin and/or other compounds known to one of skill in the art to have similar anti-coagulant properties as heparin, to prevent, inhibit or reduce clotting within the inner lumen of the vascular graft.

V. Methods of Use

The disclosed PGS-gelatin blends, PGS-PLGA blends, PGS-PVA blends, PGS-PHB blends, PGS-PET blends and cross-linked PGS preparations can be electrospun into any desired shape, such as sheets, tubes, meshes, pseudo 3-dimensional constructs. It is contemplated that the constructs may be of high porosity, low porosity, a combination of porous or non-porous. In some examples, the disclosed PGS-gelatin blends, PGS-PLGA blends, PGS-PVA blends, PGS-PHB blends, PGS-PET blends and cross-linked PGS preparations are electrospun into sheets to form fibers, random meshes, aligned sheets, cylindrical tubes, or pseudo 3-dimensional constructs, such as shapes to mimic organs. In some examples, complex shapes such as those mimicking organs are formed by combining different electrospinning techniques. Fabrication by electrospinning rather than traditional methods permits creation of thin, fibrous, anisotropic constructs which can improve cell response. The disclosed methods of electrospinning can be used to create highly porous scaffolds to mimic ECM. These structures are especially useful for applications in soft and elastomeric tissues. It is contemplated that the disclosed methods can be used to generate constructs/scaffolds used to guide host tissue remodeling in many different tissues, including any tissue that has progenitor cells. The biodegradable scaffold can be used to facilitate tissue regeneration in vivo by providing a structural frame for which tissue regeneration can occur. In some examples, the PGS is electrospun such that it allows and facilitates the infiltration of host cells including progenitor cells. In some examples, the composition is such that it allows and facilitates host remodeling of the PGS, so that eventually the polymeric structure is replaced by the desirable host tissue. It is contemplated that the methods of fabrication disclosed herein can be modified as desired by one of ordinary skill in the art to fabricate a graft with the appropriate dimensions and features depending upon tissue which is to be replaced.

In some particular examples, the generated tissue constructs are for the replacement and/or repair of damaged native tissues. For example, the disclosed constructs are contemplated to be implantable for tensile load bearing applications, such as being formed into tubes and implanted as artery interpositional grafts or artery bypass grafts as well as other tensile load bearing applications. Fiber morphology can be varied. For example, the degree of fiber fusion can be varied based on the ratio of PGS pre-polymer:PLGA, PGS pre-polymer:PVA blends, PGS pre-polymer:PHB blends, PGS pre-polymer:PET blends or PGS:gelatin. Fiber fusion can be useful to render sheets watertight but still retain superior strength to casted sheets. By producing stronger PGS constructs, this method enables PGS to be directly implanted in subjects into load bearing environments without additional mechanical support. Uses range from sheets for hernia repair, prolapse, and wound dressings, to complex tubes for blood vessel, nerve and trachea repair. Additionally, aligned random transition spinning may be useful for ligament-bone interfaces. Finally, disclosed chemically cross-linked PGS constructs are solvent resistant permitting templating techniques for complex structures. In some examples, an applicable templating technique is templating to produce microchannels: PGS is electrospun around plastic microfibers such as suture (the "template"), then the plastic microfibers are dissolved with organic solvent to leave empty space in their place.

In some examples, a disclosed vascular graft can be used to form a blood vessel in vivo. For example, a disclosed vascular graft can be implanted into a subject in need of vascular graft at the desired location to form a conduit in which blood may initial flow and ultimately become transformed into a blood vessel by action of the subject's own cells, such as blood vessel of less than 10 mm, such as less than 6 mm or less than 4 mm, including, about 9 mm, about 8 mm, about 7 mm, about 6 mm, about 5 mm, about 4 mm, about 3 mm, about 2 mm, or about 1 mm, or as low as 0.5 mm. In some examples, the vascular graft is used as a coronary or a peripheral arterial graft or venous grafts or lymphatic vessels. In some examples, the vascular graft is used as an arteriovenous shunt for dialysis access where "maturation" of 2-3 months is common.

The following examples are provided to illustrate certain particular features and/or embodiments. These examples should not be construed to limit the disclosure to the particular features or embodiments described.

EXAMPLES

Example 1

This example demonstrates PGS:gelatin blend electrospinning with thermo-curing results in fibers with desirable properties that can be used to form various scaffolds.

Figure 9:
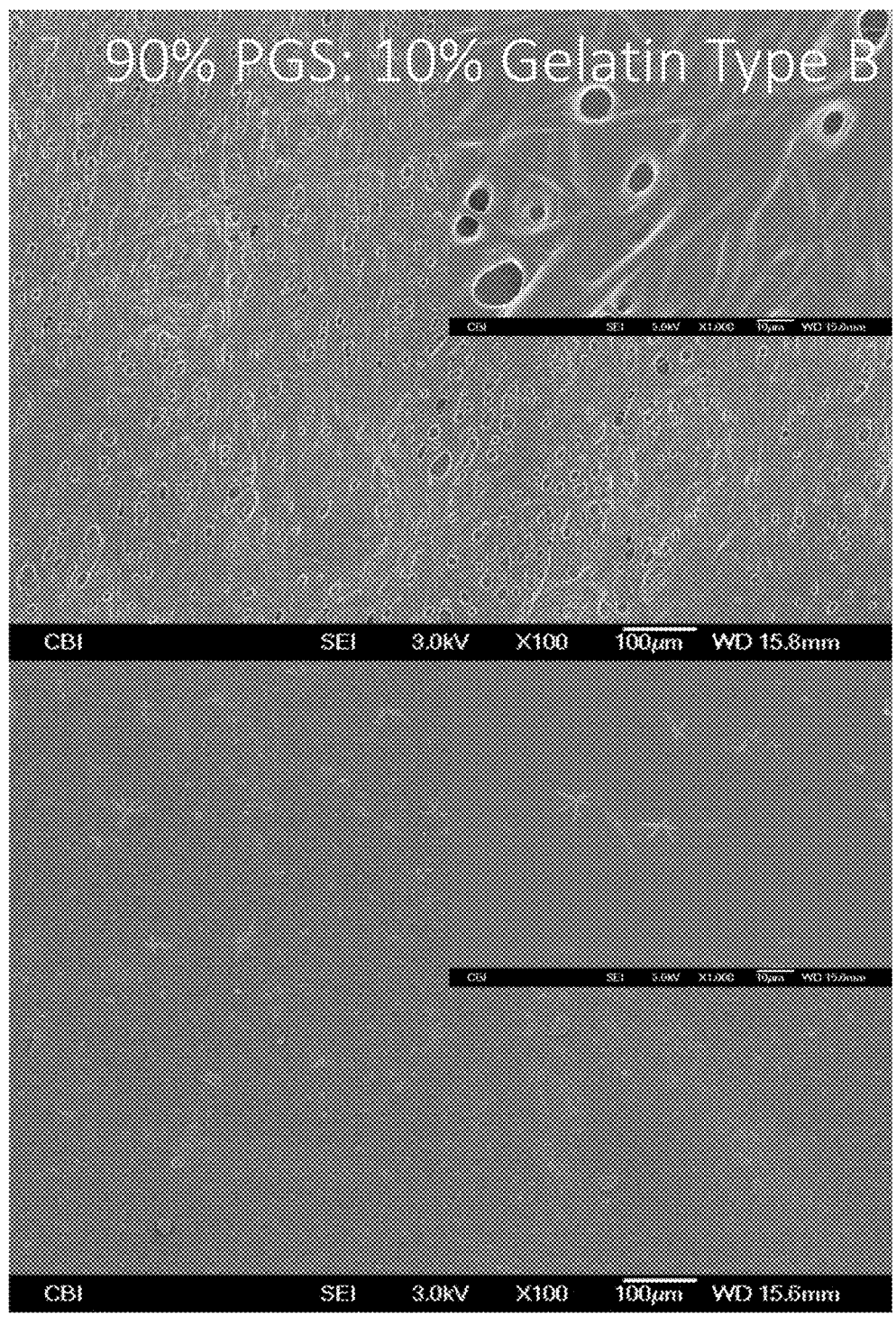
FIG. 9 is a pair of scanning electron microscope (SEM) images of PGS-gelatin (Type B) fibers with 90% PGS content, before (top) and after (bottom) heat crosslinking 130° C. for 24 hours.
Figure 11:
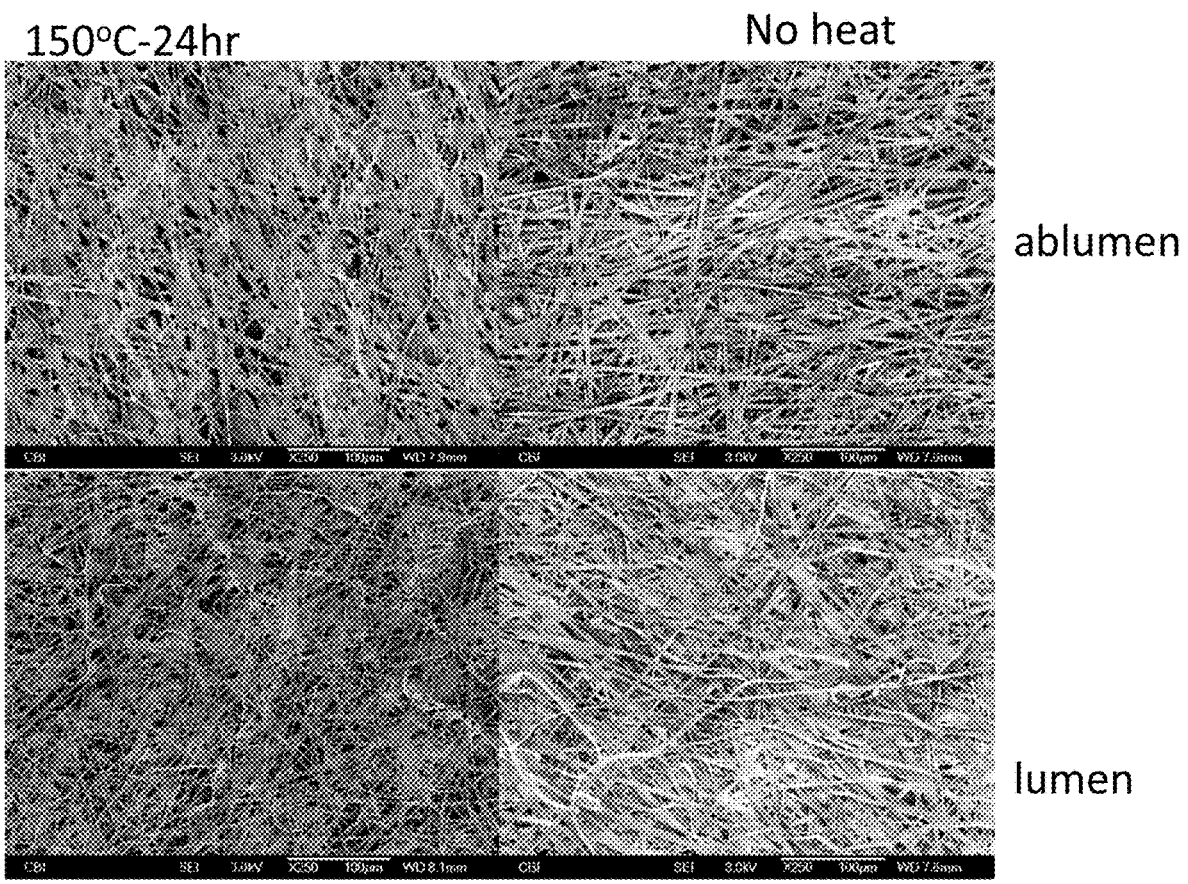
FIG. 11 is a series of SEM images illustrating 50% PGS:50% gelatin B blend electrospun onto a mandrel.
Figure 12:
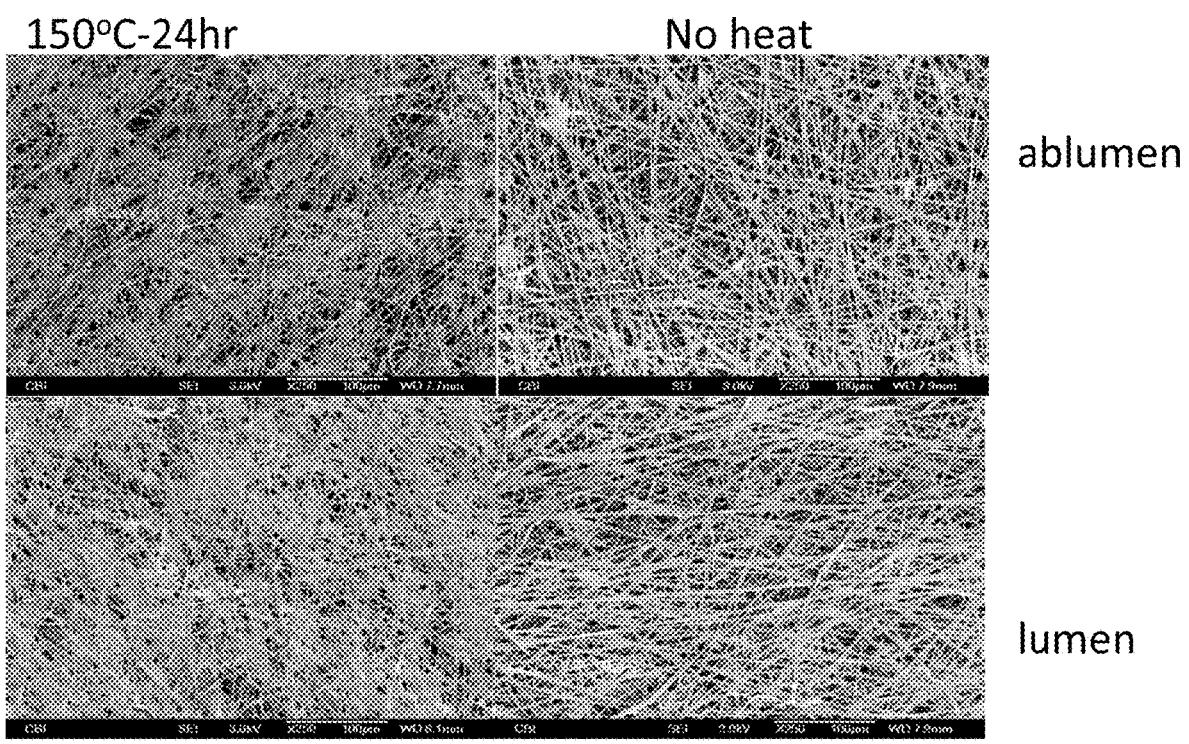
FIG. 12 is a series of SEM images illustrating 63% PGS:37% gelatin B blend electrospun onto a mandrel.
Figure 13:
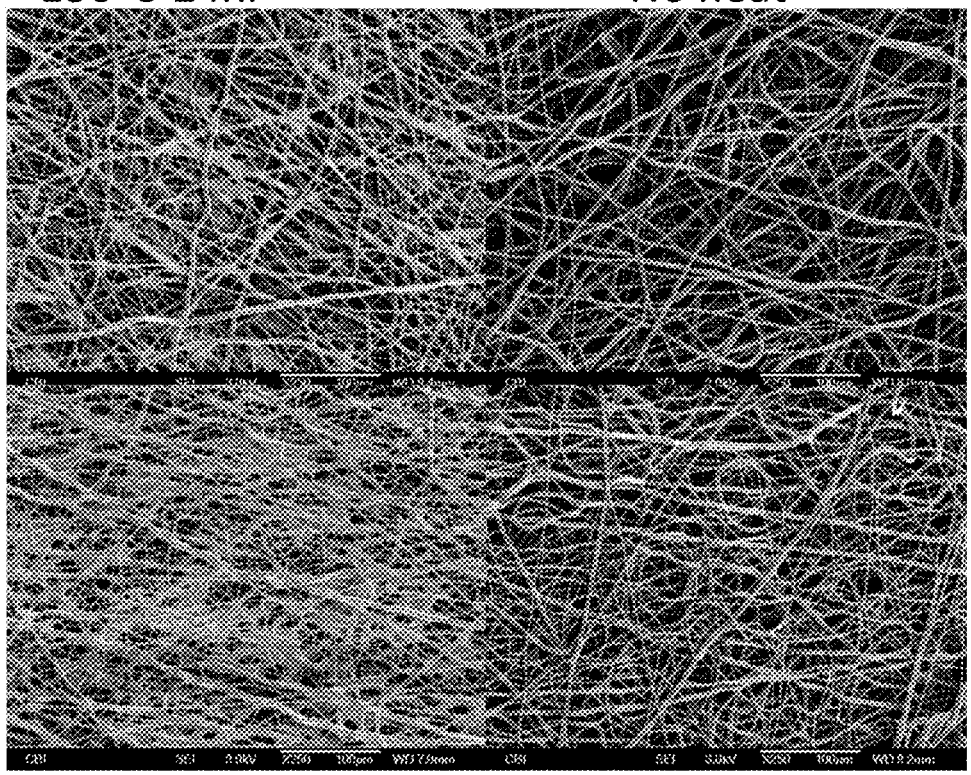
FIG. 13 is a series of SEM images illustrating 71% PGS:29% gelatin B blend electrospun onto a mandrel.
Figure 14:
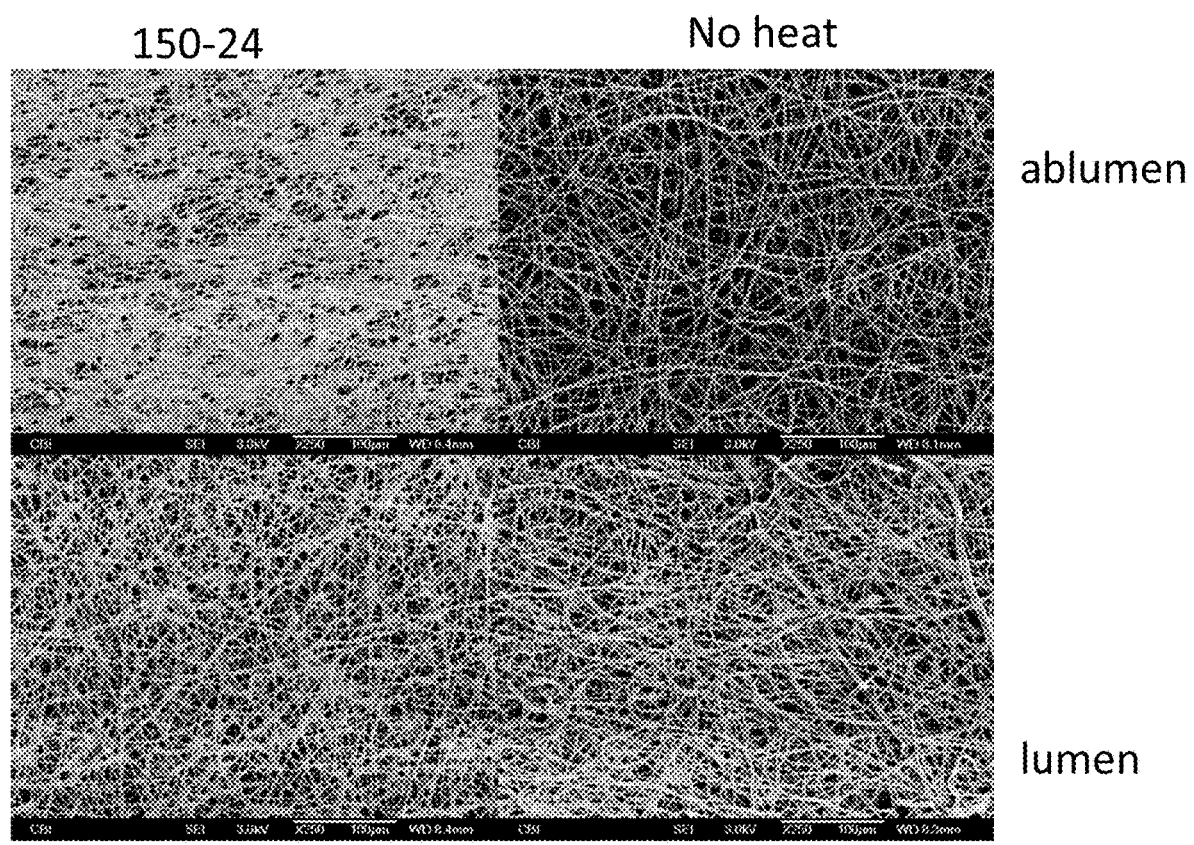
FIG. 14 is a series of SEM images illustrating 77% PGS:23% gelatin B blend electrospun onto a mandrel.

As illustrated in FIG. 1, an open collector was used for collecting PGS-gelatin (Type B) fibers (FIGS. 2-9). A benefit of this collector was that the fibers were not pressed against a solid surface which could increase fiber fusion. FIGS. 2-9 provide SEM images of fibers before (top) and after (bottom) heat crosslinking 130° C. for 24 hours. PGS content increased from 25% (FIG. 3) to 50% (FIG. 4) to 63% (FIG. 5) to 71% (FIG. 6) to 77% (FIG. 7) to 83% (FIG. 8) to 90% (FIG. 9). Low PGS content yielded non-uniform fiber morphology and ribbon-like fibers. As PGS content increased, fibers became more round and uniform, but with increased fusion; especially after curing.

Figure 16A:
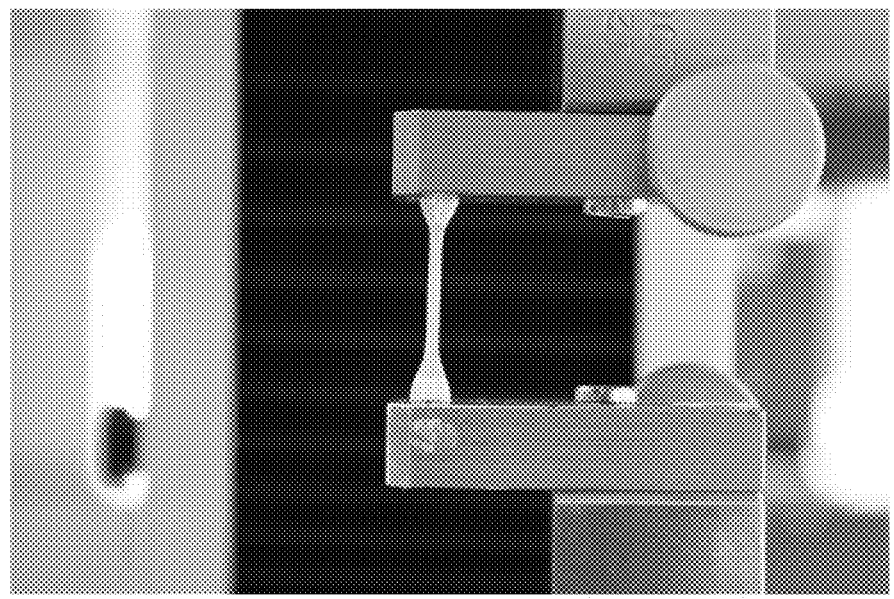
FIGS. 16A-16B includes a digital image (FIG. 16A) and graph (FIG. 16B) illustrating the tensile mechanical testing of PGS-gelatin sheets and results, respectively.
Figure 16B:
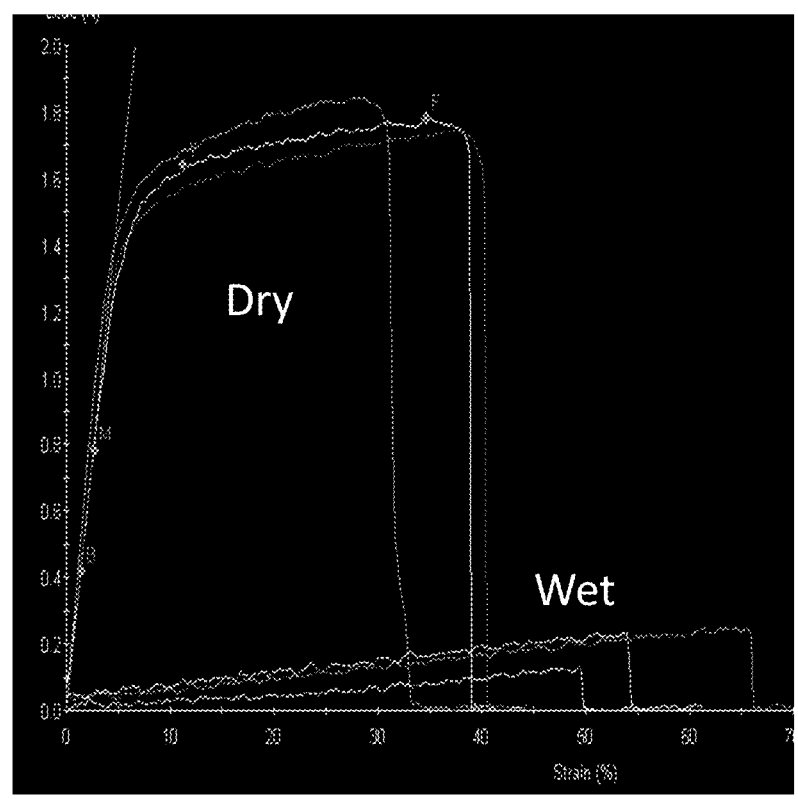

FIGS. 10A and 10B are digital images illustrating that PGS-gelatin blends formed into simple shapes by electrospinning the blends onto a mandrel. FIGS. 11-14 are SEM images illustrating various PGS-gelatin blends electrospun onto a mandrel. FIG. 15 includes a series of SEM images illustrating that complex shapes can be electrospun and retain structure as well as fiber morphology with the disclosed methods. FIG. 16 is a digital image (A) and graph (B) illustrating the tensile mechanical testing of 50% PGS-50% gelatin type B sheets (cured 130° C. for 24 hours) and results. Autoclaves are commonly used to sterilize medical implants and do not leave residue like ethylene oxide treatment. Many common biocompatible polyesters melt when autoclaved and require an alternate sterilization technique. PGS-gelatin is stable when autoclaved after sufficient curing (FIG. 17).

These studies indicate that the disclosed methods of electrospinning PGS:gelatin blend with thermo-curing results in fibers with desirable properties that can be used to form various scaffolds and are tolerant of autoclaving.

Example 2

This example demonstrates vascular grafts formed of electrospun, chemically cross-linked PGS with or without PLGA contained in the final product.

An advantage of PGS vascular grafts is that PGS is completely absorbed and replaced by artery-like tissue in 3 months. This performance is unique to PGS. However, previously non-electrospun PGS was implanted as a vascular graft, but the graft required a girdle of polycaprolactone to be strong enough for implantation. Prior to the studies disclosed herein, data was not available demonstrating that PGS could be implanted as a vascular graft without additional mechanical support.

Figure 19:
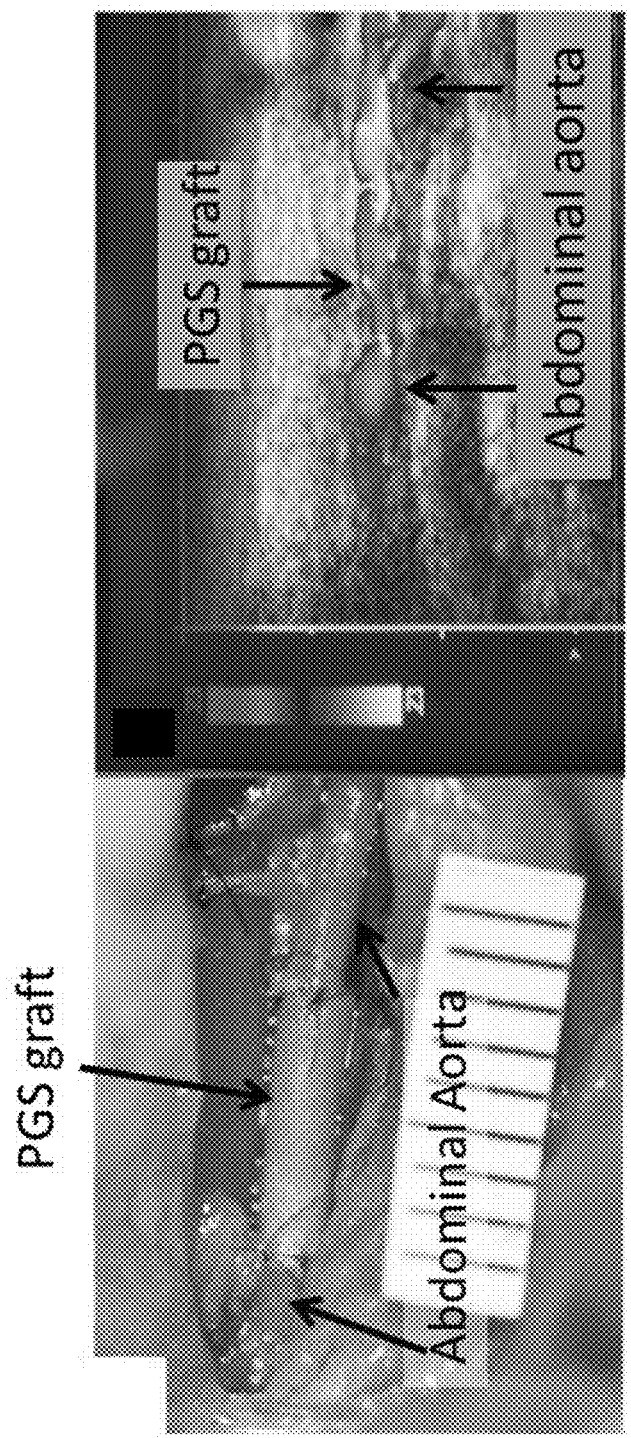
FIG. 19 is a pair of digital images of a PGS graft implanted in rat abdominal aorta (left panel) and a laser Doppler ultrasound image showing blood flow through the graft (right panel).
Figure 21:
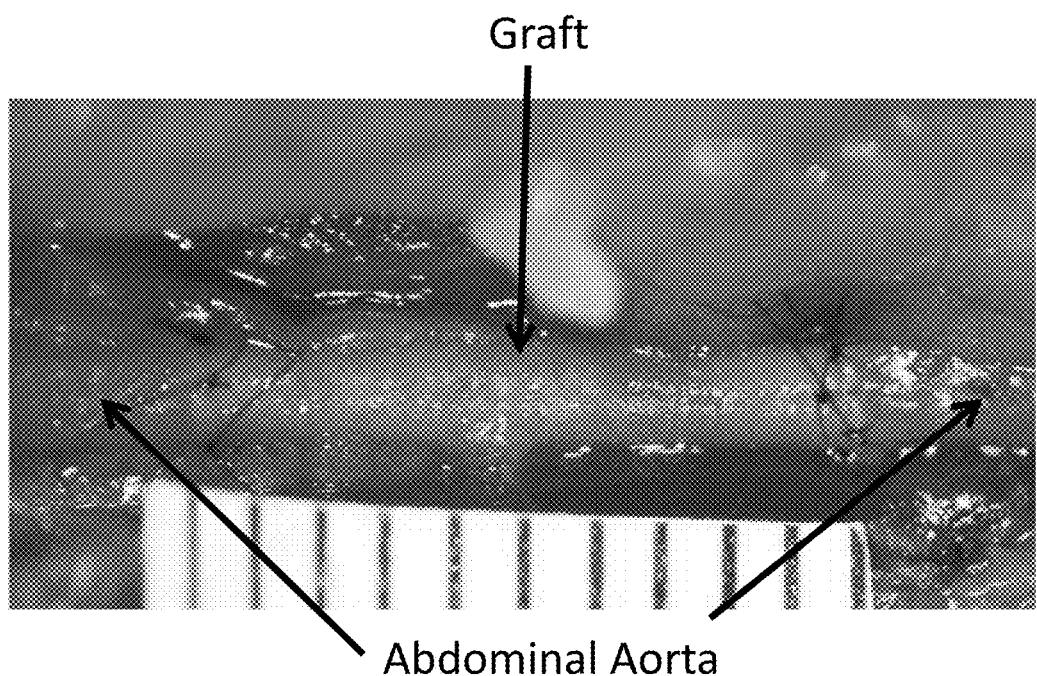
FIG. 21 is a digital image of a PGS-PLGA graft implanted in rat abdominal aorta.

The electrospinning technique described herein produced PGS implants strong enough to be implanted as a vascular graft without an external support. Further, it is believed to be the first use of an electrospun blend of PGS-PLGA by conventional electrospinning (not core-shell or dual nozzle electrospinning). FIG. 18 is a schematic illustrating the technique. The method included producing fibrous constructs from PGS by (1) blending PGS prepolymer with PLGA and a chemical cross-linker, (2) electrospinning, (3) dissolving the PLGA with organic solvent, and (4) quenching unreacted chemical cross-linker and removing other impurities with ethanol and water washes. The electrospinning precursor solution contained PGS prepolymer (125 mg/mL), PLGA (55 mg/mL), lysine triisocyanate (11.5 mg/mL), and lithium bromide (300 mM) dissolved in tetrahydrofuran. PGS prepolymer was made by polycondensation of sebacic acid and glycerol as described by Wang Y et al. (*Nat Biotechnol.,* 20(6):602-606, 2002) which is hereby incorporated by reference in its entirety. PGS prepolymer was blended with PLGA in the electrospinning precursor solution because PLGA easily forms electrospun fibers. PLGA incorporated PGS prepolymer into its fibers as they formed, yielding blended PGS prepolymer-PLGA fibers. The chemical cross-linker lysine triisocyanate was mixed into the electrospinning precursor solution to chemically cross-link the PGS prepolymer into PGS. Lithium bromide (300 mM) was also added to improve the electrical conductivity of the solution, thereby further promoting fiber formation. Standard electrospinning techniques were used to electrospin the precursor solution into microfibers. In brief, the precursor was loaded into a syringe, and the syringe needle was connected to a positive voltage source. The needle was pushed through a hole in an acrylic box, and on the other end of the box an aluminum plate was connected to a negative voltage source. Electrospinning was achieved by turning the voltage sources on and using a syringe pump to infuse the precursor solution into the acrylic box. Electrospun fibers were collected onto a rotating cylindrical mandrel placed between the needle and the aluminum plate to form a tube shape. PGS prepolymer was cross-linked into PGS via lysine triisocyanate over the course of 48 hours. PLGA was removed by washing the construct in tetrahydrofuran (i.e., two 3-hour washes followed by a 12 hour wash). FIGS. 19-21 are digital images of resulting PGS grafts implanted in rats confirming that the disclosed PGS constructs could be formed into tubes and implanted as artery interpositional grafts. FIG. 19 (left panel) is an image of a PGS vascular graft implanted to replace a section of abdominal aorta in rats; this image was taken immediately after surgery. FIG. 19 (right panel) is a laser Doppler ultrasound image showing blood flow through the graft at 7 weeks after implantation demonstrating that the graft remained opened after 7 weeks in vivo. FIG. 20, left panel, shows a PGS graft was completely absorbed and replaced by artery-like tissue. This performance is a unique advantage of PGS. FIG. 20, top right panel, is an image of the middle of the graft which grossly resembles a native artery. FIG. 20, bottom right panel, is an image of a microscope slide of the wall of artery-like tissue that had replaced the vascular graft, illustrating that PGS was not detected in such sample. FIG. 21 is a digital image of a PGS-PLGA blend graft implanted in a rat abdominal aorta illustrating that grafts made from PGS blended with PLGA can be used successfully as well. In this embodiment, the step in which PLGA was dissolved was omitted.

Figure 22:
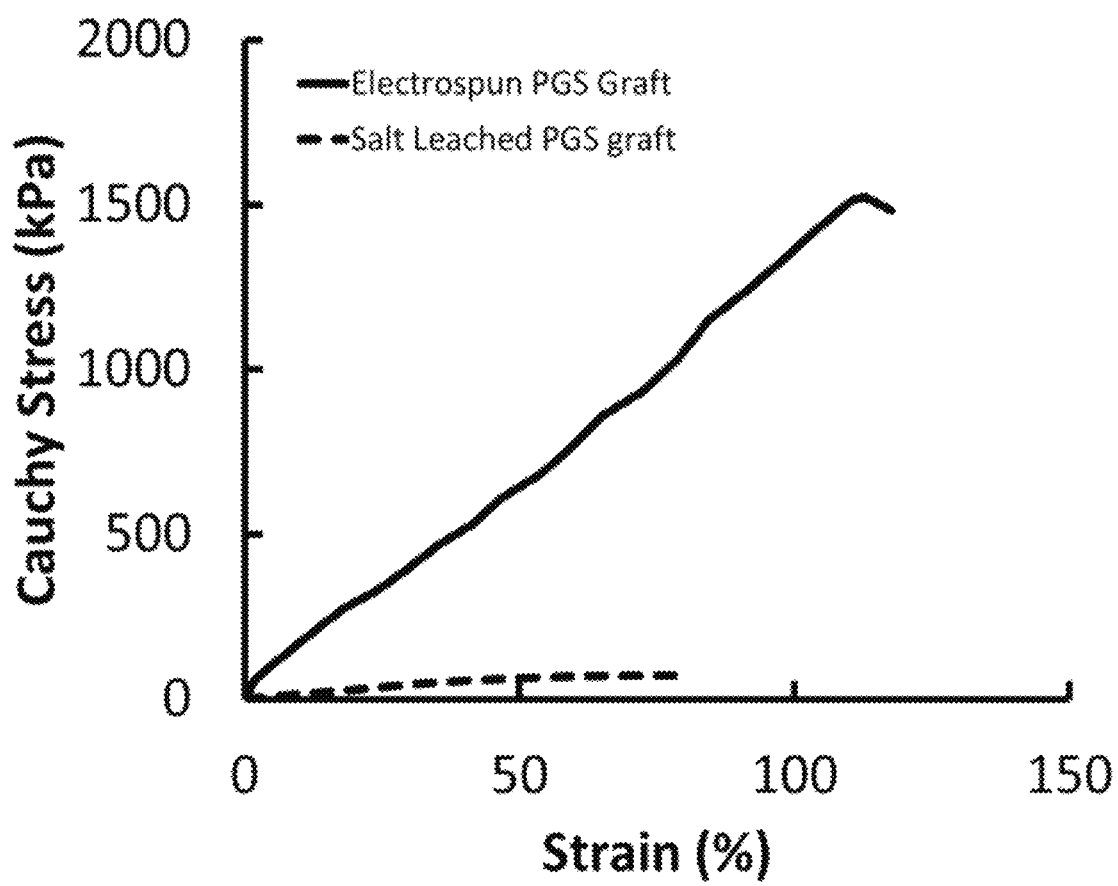
FIG. 22 is a graph illustrating electrospun PGS is stronger than solvent casted/salt leached PGS.

FIG. 22 illustrates electrospun PGS is stronger than solvent casted/salt leached PGS. Representative stress-strain curves of electrospun PGS tubular grafts and solvent casted/salt leached PGS tubular grafts. Electrospun PGS grafts are stiffer (Tensile elastic modulus=1.25 vs. 0.090 MPa) and have superior ultimate tensile stress (1.5 vs. 0.072 MPa) than solvent casted/salt leached PGS grafts. Tubes were cut into rings and pulled apart using pins as described by Wu W et al. (Nat Med. 18(7):1148-53, 2012).

Example 3

This example demonstrates PGS:PVA, PHB or PET blends with desirable properties that can be used to form various scaffolds were prepared by electrospinning with thermo-curing.

PGS cannot be electrospun alone due to low molecular weight and glass transition temperature. Thus, PVA, PHB or PET was used as a carrier polymer.

a. PGS:PVA Blend

PVA was selected as a carrier polymer because it: 1) is water soluble, avoiding organic solvents for the removal; 2) does not melt at curing temperatures of 100-150° C., avoiding fiber coalescence; 3) it possesses suitable properties to be electrospun; and 4) is biocompatible.

i. Methods

Solutions: 16 w/v % solutions of PGS prepolymer-PVA were prepared in hexafluoroisopropanol. Mass ratios of PGS prepolymer-PVA were examined at 50:50, 55:45, and 60:40 for quality of electrospun fiber morphology.

Electrospinning:

Aluminum Plate Stationary Collector:

Solution was pumped through 22 gauge needles at 29 µL/min with 10 kV+ placed on needle. The collector, aluminum plate, was placed 30 cm from the needle with 10 kV− was applied.

Mandrel Collector:

Solution was pumped through 22 gauge needles at 29 µL/min with 10 kV+ placed on needle. The collector, an aluminum mandrel or glass pipette, was placed 30 cm from the needle. A horizontal needle with 10 kV− applied was placed 60 cm from the syringe needle.

Crosslinking:

Electrospun constructs were crosslinked by thermal curing for at least 24 hrs at 120° C.

PVA-Monomer Removal:

Thermal-cured samples were washed with water and ethanol at different ratios for different amounts of time to remove the carrier polymer.

Mass Loss/Fourier Transformed Infrared Spectroscopy (FTIR):

Samples were weighed and FTIR was performed before and after PVA-monomer removal protocols.

Mechanical Testing:

Wet samples were cut in dog bone shapes for cyclic and strain to failure tensile testing.

ii. Results

Figure 23:
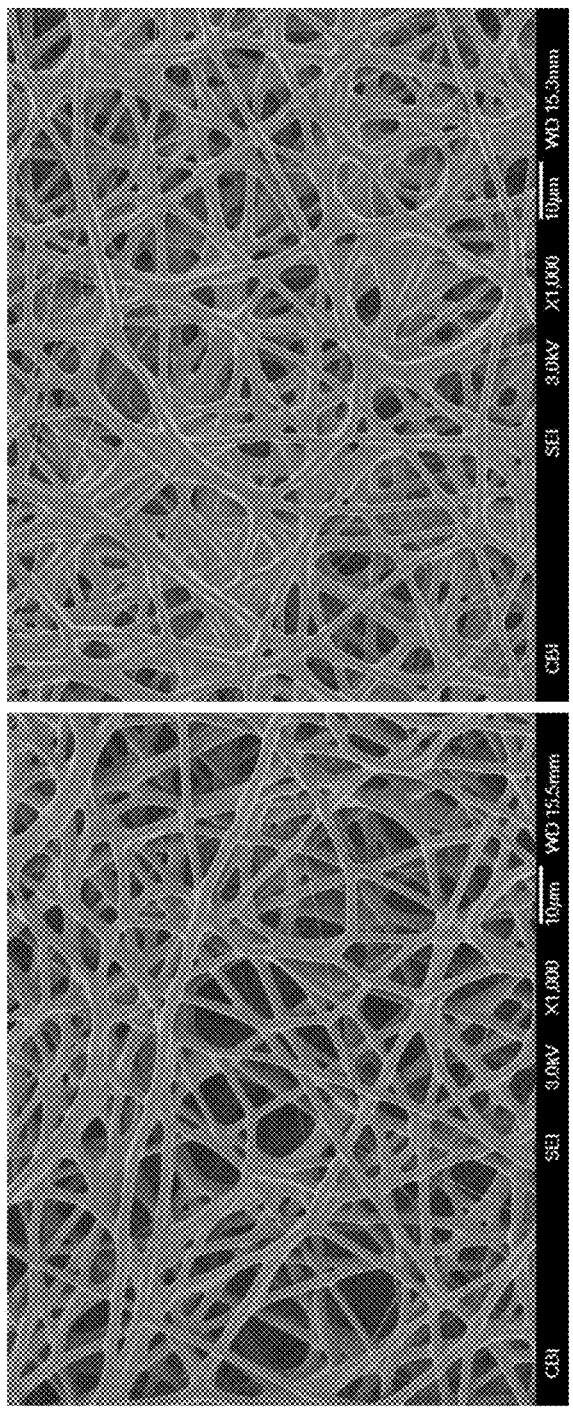
FIG. 23 is a pair of SEM images illustrating the ability to electrospin PGS-PVA fibers on a standard stationary plate and crosslink with heat without losing fibrous structures.
Figure 25:
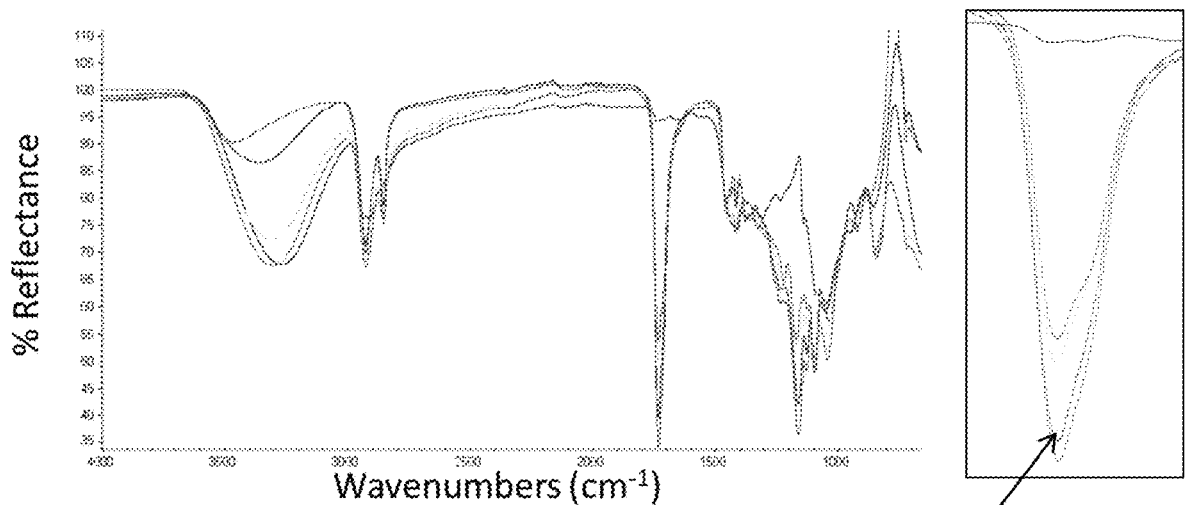
FIG. 25 provides the Fourier transformed infrared (FTIR) spectroscopy and mass loss analysis results of the PGA-PVA electrospun fibers demonstrating removal of a significant amount of the PVA carrier.

FIG. 23 illustrates the ability to electrospin PGS-PVA fibers on a standard stationary plate and crosslink with heat without losing fibrous structures. FIG. 24 (top panel) illustrates the ability to electrospin PGS-PVA fibers on a mandrel. In particular, FIG. 24 (top panel) provides a digital picture of a sheet of PGS-PVA spun at a ratio of 55:45 PGS:PVA (55 PGS-PVA) electrospun onto an aluminum mandrel. FIG. 24 (bottom panel) provides a series of SEM images illustrating fiber morphology after electrospinning, crosslinking, and washing for 3 different blends of PGS-PVA. FIG. 25 provides the FTIR and mass loss analysis of the fibers demonstrating removal of a significant amount of the PVA carrier. FIG. 26 illustrates the mechanical testing of the 55 PGS-PVA fibers showing a soft material with tunable tensile properties based on crosslinking. FIG. 27 demonstrates the ability to fabricate fibrous tubes from PGS-PVA and PGS-PHB blends by electrospinning and heat crosslinking. In panel B, fibers are shown to deposit unevenly on the unfixed end of the glass mandrel. Panel C depicts a mandrel coated with PGS-PVA fibers after electrospinning. The annotations denote allocation of PGS fiber tubes for further processing. Three grafts were obtained from the fibers deposited on one glass mandrel. Dotted lines indicate the location where a small ring (1 to 2 mm thick) was taken for SEM imaging.

b. PGS-PHB

PHB was selected as carrier polymer because it is does not melt at curing temperatures of 100-150° C.; possesses suitable properties to be electrospun; has a high mechanical modulus, improving compression resistance of electrospun conduits; and degrades slower than PGS, providing a second blending component that can be used to tune degradation profile.

i. Methods

Solutions:

12 w/v % solutions were prepared from stock solutions of 8% PHB and 50% PGS prepolymer in HFIP at a ratio of 2PGS:1PHB.

Electrospinning:

Mandrel Collector:

Solution was pumped through 22 gauge needles at 29 µL/min with 10 kV+ placed on needle. The fibers were collected on a glass pipette placed 30 cm from the needle. A horizontal needle with 10 kV− applied was placed 60 cm from the syringe needle.

Crosslinking:

Electrospun constructs were crosslinked by thermal curing for at least 24 hrs at 120° C. Other times and temperatures are being conducted to optimize mechanical properties and PVA removal.

ii. Results

FIGS. 27A-E demonstrate the ability to fabricate fibrous tubes from PGS-PHB blends by electrospinning and heat crosslinking.

c. PGS-PET

Polyethylene terephthalate (PET) was chosen because it is does not melt at curing temperatures of 100-150° C.; possesses suitable properties to be electrospun; has a high mechanical modulus, improving tension and compression resistance of electrospun implants; degrades slower than PGS, providing a second blending component that can be used to tune degradation profile; and is an FDA approved material used for vascular grafts.

i. Methods

Solutions:

17 to 23 w/v % solutions of PGS-PET were prepared in hexafluoroisopropanol (HFIP). Mass ratios of PGS prepolymer:PET were examined at 70:30, 60:40, and 50:50.

Electrospinning:

Solution was pumped through a 22 gauge needle and could be drawn into fibers using a wide range of parameters. Two examples shown below in Table 2:

TABLE 2

Electrospinning parameters for PGS prepolymer-PET

| PGS:PET Ratio | Infusion rate (μL/min) | Distance from syringe needle to mandrel (cm) | Mandrel/ Outer Diameter | Distance from syringe needle to negative potential source (cm) | Conductor imparted with negative potential | Mandrel rotational speed |
|---|---|---|---|---|---|---|
| 60:40 | 29 | 30 | Stainless Steel/6.35 mm | 50 | 1 mm diameter stainless steel rod, ~1' long | Alternate between 100 and 300 RPM every 100 μL |
| 50:50 | 19 | 5 to 6 | Aluminum/ 1" | 10.75 | Razor blade | 210 |

Crosslinking:

Electrospun constructs were crosslinked by thermal curing for 4 hrs at 80° C., 4 hrs at 90° C., 12 hrs at 100° C., and 24 h at 150° C.

PET-Monomer Removal (Optional):

Thermal-cured samples were washed in a graded series of ethanol solutions (20% EtOH in water, 40% EtOH, 60%, 80%, 100%; 20 minute rinses each), then washed with a graded series of HFIP solutions to dissolve and remove the PET (20% HFIP in EtOH, 40%, 60%, 80%, 100%; 20 minute rinses each, with 100% repeated overnight). To remove all residual HFIP residue, the rinse series was then performed in reverse order.

Mass Loss/Fourier Transformed Infrared Spectroscopy (FTIR):

Samples were weighed and FTIR was performed before and after PET-monomer removal protocols.

ii. Results

Figure 28:
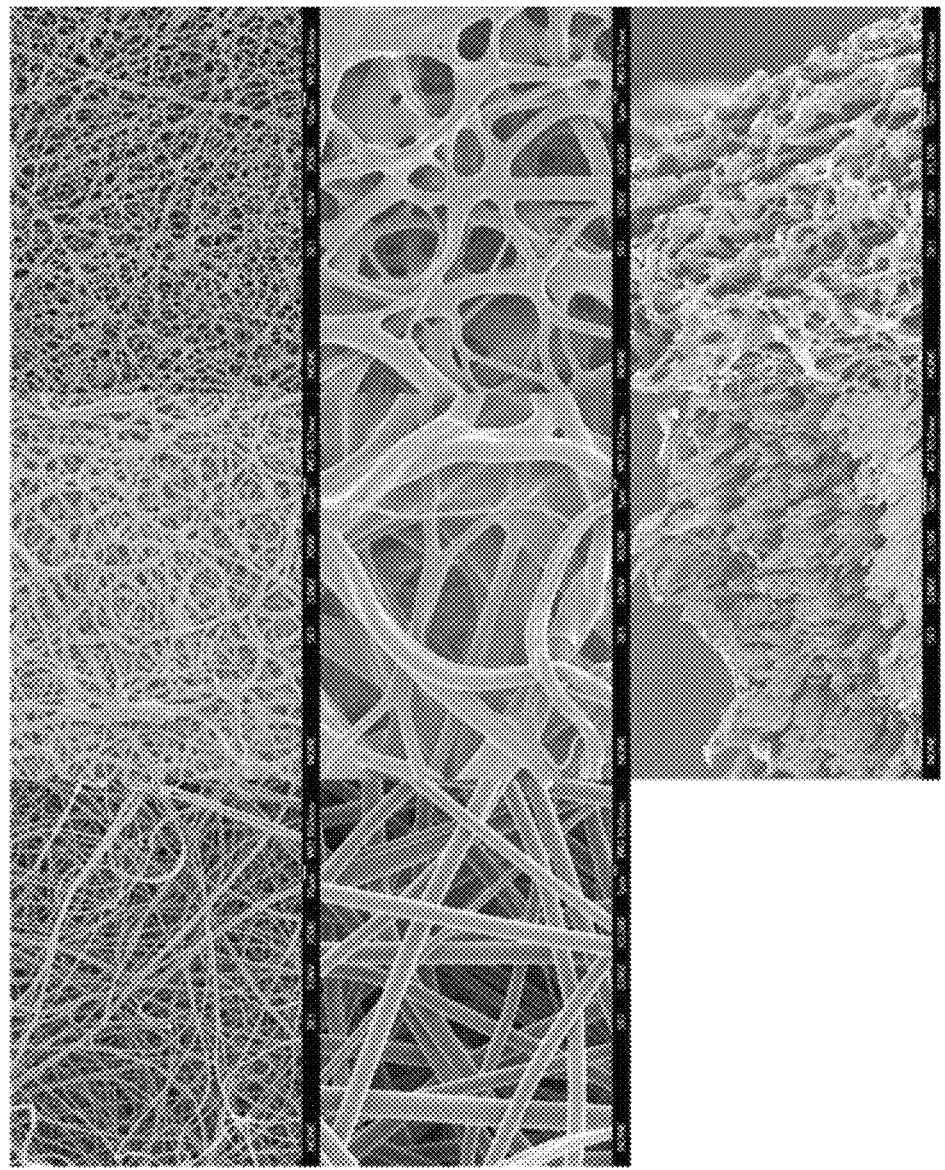
FIG. 28 is a series of SEM images illustrating PGS-PET fibers.
Figure 29:
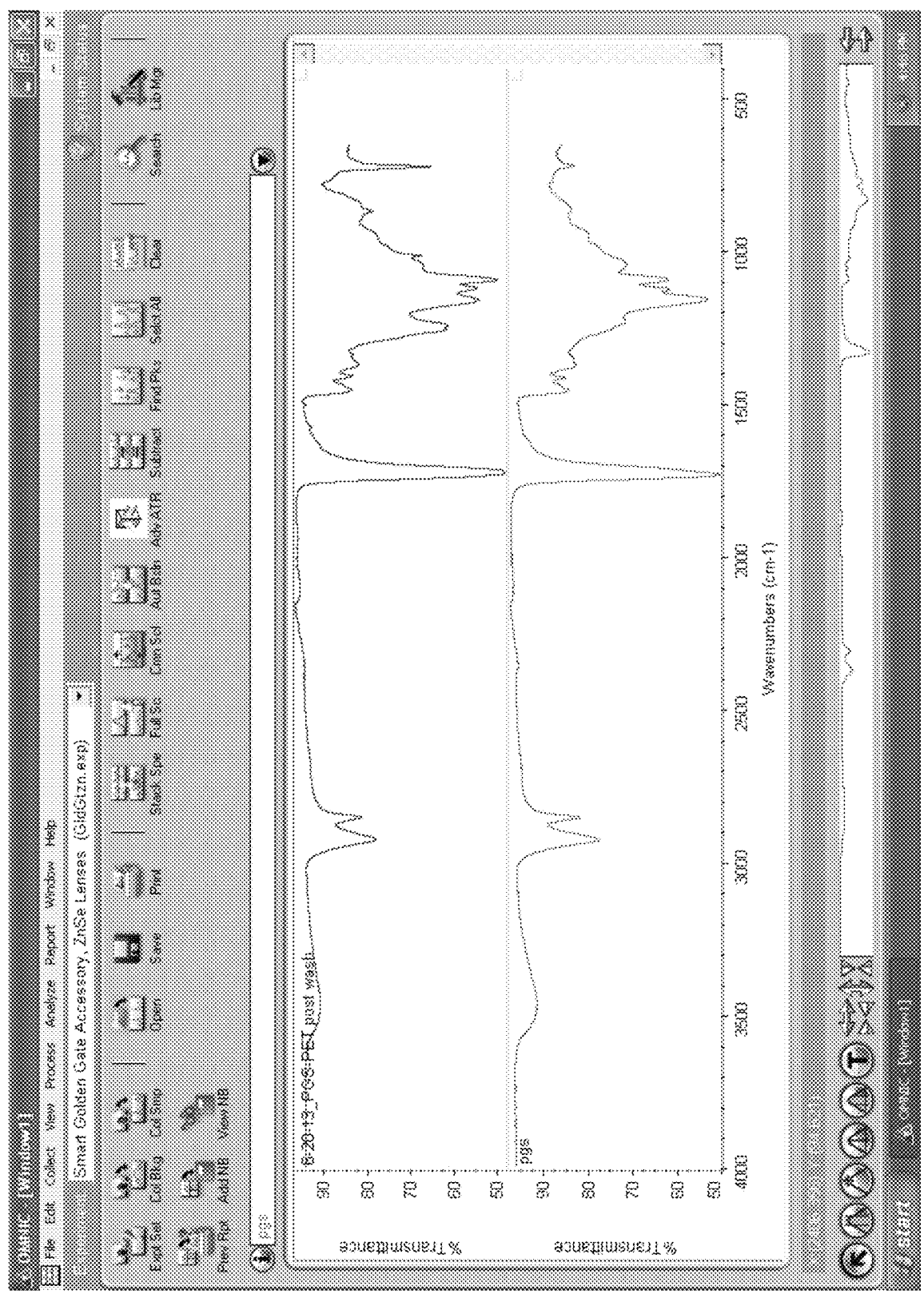
FIG. 29 is a FTIR analysis of PGS-PET fibers illustrating the absence of PET residues on the formed fibers (FIG. 28). PGS fibers formed from PGS-PET electrospinning (top tracing) show similar spectra to pure PGS (bottom tracing) and lack aromatic stretches indicative of PET.

The resulting fibers are shown in FIG. 28. FTIR analysis indicates absence of PET residues on the formed fibers (FIG. 29). PGS fibers formed from PGS-PET electrospinning (top tracing) show similar spectra to pure PGS (bottom tracing) and lack aromatic stretches indicative of PET.

These studies illustrate that the disclosed methods allow PGS material properties (elastic mechanical properties, tunable mechanical properties, biocompatible, biodegradable and thermoset) to be maintained while also gaining the benefits of electrospinning processing. The use of electrospinning resulted in fibers with anisotropic structure and such fibers mimic the extracellular matrix while permitting nutrient and waste transport. Further, the disclosed methods generated fibers stronger than those formed by other processes (e.g., solvent casting-salt leaching), thereby enabling PGS to be sutured for load bearing implantations. It is believed that this is the first report of suturable PGS.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A scaffold made from a fibrous construct prepared by:
    electrospinning a poly(glycerol sebacate) (PGS) prepolymer solution comprising PGS prepolymer blended with a heat-resistant carrier polymer into a PGS prepolymer construct, wherein the electrospinning does not include core-shell electro spinning;
    cross-linking the electrospun PGS prepolymer construct into a PGS construct by heat curing the electrospun PGS prepolymer and heat-resistant carrier polymer of the PGS prepolymer construct without chemical cross-linkers; and
    removing the heat-resistant carrier polymer after the cross-linking.

2. The scaffold of claim 1, wherein the fibrous construct further comprises a pharmaceutical agent.

3. The scaffold of claim 1, further comprising cells.

4. A vascular graft comprising the scaffold of claim 1, wherein the scaffold is tubular in shape and comprises an inner luminal surface and a thromboresistant agent coating the inner luminal surface of the scaffold, thereby forming a vascular graft.

5. The vascular graft of claim 4, wherein at least 95% of the vascular graft degrades within 90 days of implantation.

6. The vascular graft of claim 4, wherein the vascular graft is cell-free.

7. The vascular graft of claim 4, wherein the vascular graft is used for forming a blood vessel with an inner diameter of less than 6 mm.

8. The vascular graft of claim 4, wherein the vascular graft is used for forming a blood vessel with an inner diameter of less than 4 mm.

9. The vascular graft of claim 4, wherein the vascular graft is used as a coronary or a peripheral arterial graft.

10. A method of fabricating a vascular graft, comprising:
   preparing a scaffold of claim 1, wherein the scaffold is tubular in shape and comprises an inner luminal surface; and
   coating the inner luminal surface of the scaffold with a thromboresistant agent, thereby forming a vascular graft, in which at least 75% of the vascular graft degrades within 90 days of implantation in a subject.

11. A composition that facilitates tissue regeneration by providing a structural frame, comprising:
   a scaffold of claim 1; and
   a thromboresistant agent coating the scaffold, thereby forming a composition that facilitates tissue regeneration in vivo by providing a structural frame.

* * * * *